US010513544B2

(12) United States Patent
Pandey et al.

(10) Patent No.: US 10,513,544 B2
(45) Date of Patent: Dec. 24, 2019

(54) GROUP A STREPTOCOCCUS VACCINE

(71) Applicant: Griffith University, Nathan, Queensland (AU)

(72) Inventors: Manisha Pandey, Nathan (AU);
Michael Batzloff, Queensland (AU);
Michael Good, Nathan (AU)

(73) Assignee: Griffith University, Nathan (AU)

( * ) Notice: Subject to any disclaimer, the term of this patent is extended or adjusted under 35 U.S.C. 154(b) by 0 days.

(21) Appl. No.: 16/398,598

(22) Filed: Apr. 30, 2019

(65) Prior Publication Data

US 2019/0256562 A1   Aug. 22, 2019

Related U.S. Application Data

(62) Division of application No. 15/304,462, filed as application No. PCT/AU2015/050174 on Apr. 15, 2015, now Pat. No. 10,301,362.

(30) Foreign Application Priority Data

Apr. 15, 2014  (AU) ................. 2014901382
Aug. 6, 2014   (AU) ................. 2014903042
Nov. 5, 2014   (AU) ................. 2014904453

(51) Int. Cl.
*A61K 39/09*    (2006.01)
*A61K 39/395*   (2006.01)
*A61K 38/48*    (2006.01)
*C07K 14/315*   (2006.01)
*C07K 16/12*    (2006.01)
*C07K 16/40*    (2006.01)
*A61K 39/00*    (2006.01)

(52) U.S. Cl.
CPC ........ *C07K 14/315* (2013.01); *A61K 38/4873* (2013.01); *A61K 39/092* (2013.01); *A61K 39/3955* (2013.01); *C07K 16/1275* (2013.01); *C07K 16/40* (2013.01); *C12Y 304/22* (2013.01); *A61K 2039/505* (2013.01); *C07K 2317/34* (2013.01); *C07K 2317/76* (2013.01)

(58) Field of Classification Search
CPC .............. A61K 39/092; A61K 34/4873; A61K 39/3955; C07K 14/315; C07K 16/1275; C07K 16/40; C07K 2317/34; C07K 2317/76; C12Y 304/22
See application file for complete search history.

(56) References Cited

U.S. PATENT DOCUMENTS

| | | |
|---|---|---|
| 2009/0010929 A1 | 1/2009 | Good et al. |
| 2009/0117113 A1 | 5/2009 | Bensi et al. |
| 2009/0162369 A1 | 6/2009 | Nordstrom et al. |
| 2017/0037087 A1 | 2/2017 | Pandey et al. |

FOREIGN PATENT DOCUMENTS

| | | |
|---|---|---|
| WO | WO 2008/003515 A1 | 1/2008 |
| WO | WO 2009/034473 A2 | 3/2009 |
| WO | WO 2010/076618 A1 | 7/2010 |
| WO | WO 2015/157820 A1 | 10/2015 |

OTHER PUBLICATIONS

Hayman et al., "Mapping the minimal murine T cell and B cell epitopes within a peptide vaccine candidate from the conserved region of the M protein of group A streptococcus," *International Immunology*, 9(11): 1723-1733 (1997).
Australian Patent Office, Notification of Transmittal of the International Search Report and the Written Opinion of the International Search Authority, or the Declarations in International Application No. PCT/AU2015/050174 (dated Jun. 12, 2015).
Australian Patent Office, Written Opinion of the International Searching Authority in International Application No. PCT/AU2015/050174 (dated Jun. 12, 2015).
Chiappini et al., "*Streptococcus pyogenes* SpyCEP Influences Host-Pathogen Interactions during Infection in a Murine Air Pouch Model," *PLoS One*, 7(7): e40411 (2012).
Good et al., "Novel Vaccine Candidates to Prevent Infection With Group A Streptococcus," *ASTMH*, 91(5): 316 (Abstract 1042) (2014).
Greenspan et al., "Defining epitopes: It's not as easy as it seems," *Nature Biotechnology*, 17: 936-937 (1999).
Lazar et al., "Transforming Growth Factor α: Mutation of Aspartic Acid 47 and Leucine 48 Results in Different Biological Activities," *Molecular and Cellular Biology*, 8(3): 1247-1252 (1988).
Pandey et al., "Long-Term Antibody Memory Induced by Synthetic Peptide Vaccination Is Protective against *Streptococcus pyogenes* Infection and Is Independent of Memory T Cell Help," *The Journal of Immunology*, 190(6): 2692-2701 (2013).
Skolnick et al., "From genes to protein structure and function: novel applications of computational approaches in the genomic era," *Trends in Biotechnology*, 18(1): 34-39 (2000).
Turner et al., "Impact of immunization against SpyCEP during invasive disease with two streptococcal species: *Steprococcus pyogenes* and *Streptococcus equi*," *Vaccine*, 27: 4923-4929 (2009).
Zinkernagel et al., "The IL-8 Protease SpyCEP/ScpC of Group A Streptococcus Promotes Resistance to Neutrophil Killing," *Cell Host Microbe*, 4(2): 170-178 (2008).

*Primary Examiner* — Sarvamangala Devi
(74) *Attorney, Agent, or Firm* — Leydig, Voit & Mayer, Ltd.

(57) ABSTRACT

The invention relates to methods of eliciting an immune response to group A streptococcal bacteria in a mammal, the method including the step of administering to the mammal an effective amount of a composition comprising an isolated p145 peptide of SEQ ID NO: 56 and/or a p145 peptide variant having an amino acid sequence at least 90% identical to SEQ ID NO: 56, and an isolated SpyCEP peptide of SEQ ID NO: 18 and/or a SpyCEP peptide variant having an amino acid sequence at least 90% identical to SEQ ID NO: 18.

4 Claims, 28 Drawing Sheets

Figure 1A:
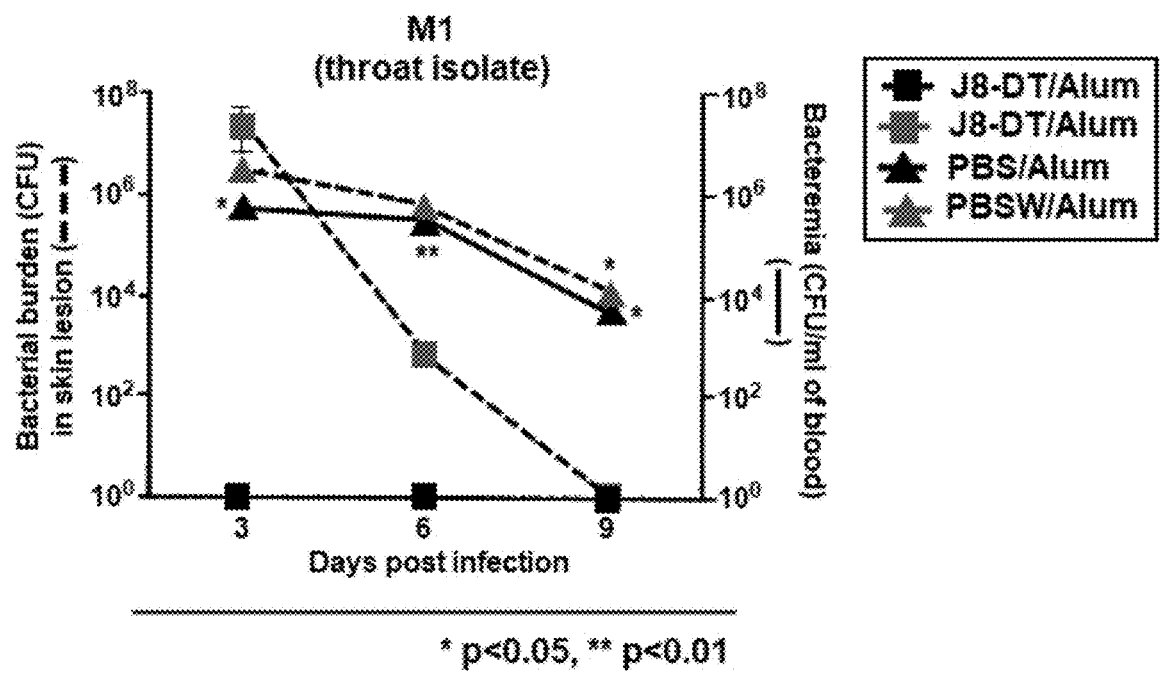

Specification includes a Sequence Listing.

GAS clinical isolate 90/31\*  J8-DT PMN−

GAS clinical isolate 90/31\*  J8-DT PMN+

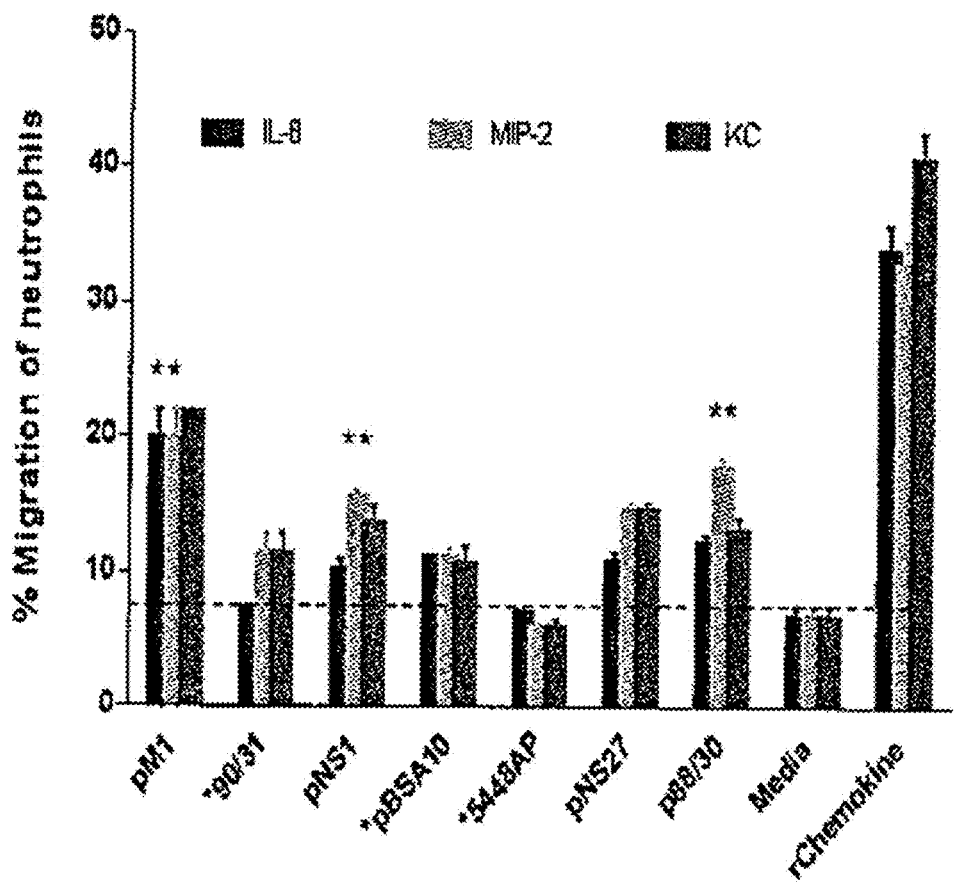
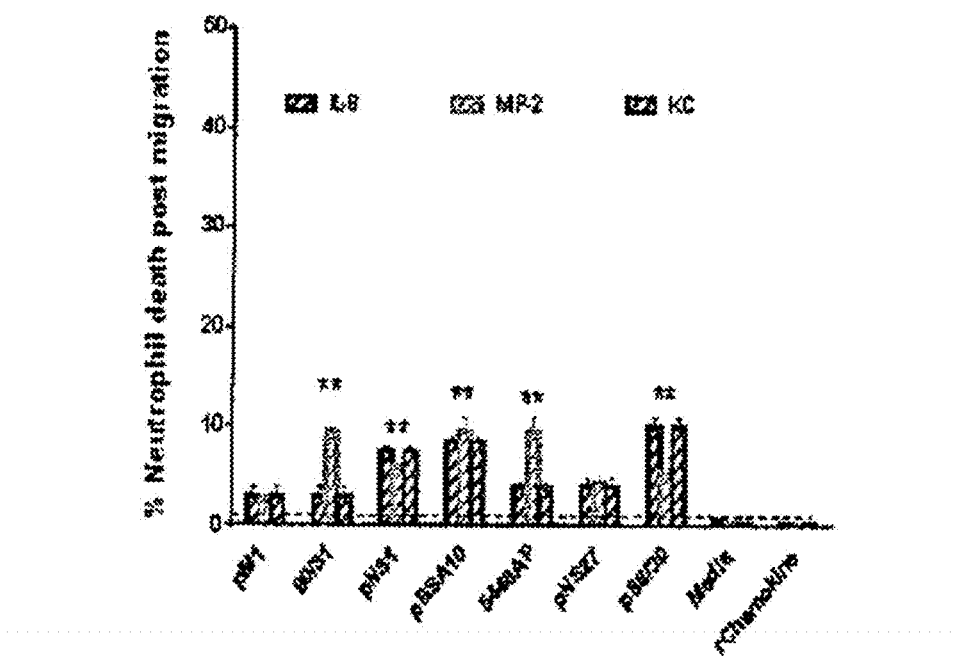
FIG. 9

| Peptide number | Sequence |
|---|---|
| 1 | DELSTMSEPTITNHAQQQAQ |
| 2 | ITNHAQQQAQHLTNTELSSA |
| 3 | HLTNTELSSAESQSPDTSQI |
| 4 | ESQSPDTSQITLKTNREKEQ |
| 5 | TLKTNREKEQSQDLVSEPTT |
| 6 | SQDLVSEPTTTELADTDSAP |
| 7 | TELADTDSAPMANTGPDATQ |
| 8 | MANTGPDATQKSASLPPVNT |
| 9 | KSASLPPVNTDVHDWVKTKG |
| 10 | DVHDWVKTKGAWDKGYKGQG |
| 11 | AWDKGYKGQGKVVAVIDTGI |
| 12 | KVVAVIDTGIDPAHQSMRIS |
| 13 | DPAHQSMRISDVSTAKVKSK |
| 14 | DVSTAKVKSKEDMLARQKAA |
| 15 | EDMLARQKAAGINYGSWIND |
| 16 | GINYGSWINDKVVFAHNYVE |
| 17 | KVVFAHNYVENSDNIKENQF |
| 18 | NSDNIKENQFEDFDEDWENF |
| 19 | EDFDEDWENFEFDAEPKAIK |
| 20 | EFDAEPKAIKKHKIYRPQST |
| 21 | KHKIYRPQSTQAPKETVIKT |
| 22 | QAPKETVIKTEETDGSHDID |
| 23 | EETDGSHDIDWTQTDDETKY |
| 24 | WTQTDDETKYESHGMHVTGI |
| 25 | ESHGMHVTGIVAGNSKEAAA |
| 26 | VAGNSKEAAATGERFLGIAP |
| 27 | TGERFLGIAPEAQVMFMRVF |

FIG. 13A

28 EAQVMFMRVFANDVMGSAES
29 ANDVMGSAESLFIKAIEDAV
30 LFIKAIEDAVALGADVINLS
31 ALGADVINLSLGTANGAQLS
32 LGTANGAQLSGSKPLMEAIE
33 GSKPLMEAIEKAKKAGVSVV
34 KAKKAGVSVVVAAGNERVYG
35 VAAGNERVYGSDHDDPLATN
36 SDHDDPLATNPDYGLVGSPS
37 PDYGLVGSPSTGRTPTSVAA
38 TGRTPTSVAAINSKWVIQRL
39 INSKWVIQRLMTVKELENRA
40 MTVKELENRADLNHGKAIYS
41 DLNHGKAIYSESVDFKDIKD
42 ESVDFKDIKDSLGYDKSHQF
43 SLGYDKSHQFAYVKESTDAG
44 AYVKESTDAGYKAQDVKGKI
45 YKAQDVKGKIALIERDLNKT
46 ALIERDLNKTYDEMIALAKK
47 YDEMIALAKKHGALGVLIFN
48 HGALGVLIFNNKPGQSNRSM
49 NKPGQSNRSMRLTANGMGVP
50 RLTANGMGVPSAFISHEFGK
51 SAFISHEFGKAMSQLNGNGT
52 AMSQLNGNGTGSLEFDSVVS
53 GSLEFDSVVSKAPSQKGNEM
54 KAPSQKGNEMNHFSNWGLTS
55 SQKGNEMNHFSNWGLTSDGY

FIG. 13B

Epitopes named as S1-S6

| Epitope ID | Amino acid numbers | Sequence |
|---|---|---|
| S1 | 175-194 | EDMLARQKAAGINYGSWIND |
| S2 | 205-224 | NSDNIKENQFEDFDEDWENF |
| S3 | 215-234 | EDFDEDWENFEFDAEPKAIK |
| S4 | 265-284 | WTQTDDETKYESHGMHVTGI |
| S5 | 325-344 | LFIKAIEDAVALGADVINLS |
| S6 | 565-584 | KAPSQKGNEMNHFSNWGLTS |

SEQUENCE LISTING

```
<160> NUMBER OF SEQ ID NOS: 64

<210> SEQ ID NO 1
<211> LENGTH: 20
<212> TYPE: PRT
<213> ORGANISM: Artificial sequence
<220> FEATURE:
<223> OTHER INFORMATION: Synthetic peptide

<400> SEQUENCE: 1

Asp Glu Leu Ser Thr Met Ser Glu Pro Thr Ile Thr Asn His Ala Gln
1               5                   10                  15

Gln Gln Ala Gln
            20

<210> SEQ ID NO 2
<211> LENGTH: 20
<212> TYPE: PRT
<213> ORGANISM: Artificial sequence
<220> FEATURE:
<223> OTHER INFORMATION: Synthetic peptide
```

```
<400> SEQUENCE: 2

Ile Thr Asn His Ala Gln Gln Gln Ala Gln His Leu Thr Asn Thr Glu
1               5                   10                  15

Leu Ser Ser Ala
            20

<210> SEQ ID NO 3
<211> LENGTH: 20
<212> TYPE: PRT
<213> ORGANISM: Artificial sequence
<220> FEATURE:
<223> OTHER INFORMATION: Synthetic peptide

<400> SEQUENCE: 3

His Leu Thr Asn Thr Glu Leu Ser Ser Ala Glu Ser Gln Ser Pro Asp
1               5                   10                  15

Thr Ser Gln Ile
            20

<210> SEQ ID NO 4
<211> LENGTH: 20
<212> TYPE: PRT
<213> ORGANISM: Artificial sequence
<220> FEATURE:
<223> OTHER INFORMATION: Synthetic peptide

<400> SEQUENCE: 4

Glu Ser Gln Ser Pro Asp Thr Ser Gln Ile Thr Leu Lys Thr Asn Arg
1               5                   10                  15

Glu Lys Glu Gln
            20

<210> SEQ ID NO 5
<211> LENGTH: 20
<212> TYPE: PRT
<213> ORGANISM: Artificial sequence
<220> FEATURE:
<223> OTHER INFORMATION: Synthetic peptide

<400> SEQUENCE: 5

Thr Leu Lys Thr Asn Arg Glu Lys Glu Gln Ser Gln Asp Leu Val Ser
1               5                   10                  15

Glu Pro Thr Thr
            20

<210> SEQ ID NO 6
<211> LENGTH: 20
<212> TYPE: PRT
<213> ORGANISM: Artificial sequence
<220> FEATURE:
<223> OTHER INFORMATION: Synthetic peptide

<400> SEQUENCE: 6

Ser Gln Asp Leu Val Ser Glu Pro Thr Thr Glu Leu Ala Asp Thr
1               5                   10                  15

Asp Ser Ala Pro
            20

<210> SEQ ID NO 7
<211> LENGTH: 20
<212> TYPE: PRT
<213> ORGANISM: Artificial sequence
<220> FEATURE:
```

-continued

<223> OTHER INFORMATION: Synthetic peptide

<400> SEQUENCE: 7

Thr Glu Leu Ala Asp Thr Asp Ser Ala Pro Met Ala Asn Thr Gly Pro
1               5                   10                  15

Asp Ala Thr Gln
            20

<210> SEQ ID NO 8
<211> LENGTH: 20
<212> TYPE: PRT
<213> ORGANISM: Artificial sequence
<220> FEATURE:
<223> OTHER INFORMATION: Synthetic peptide

<400> SEQUENCE: 8

Met Ala Asn Thr Gly Pro Asp Ala Thr Gln Lys Ser Ala Ser Leu Pro
1               5                   10                  15

Pro Val Asn Thr
            20

<210> SEQ ID NO 9
<211> LENGTH: 20
<212> TYPE: PRT
<213> ORGANISM: Artificial sequence
<220> FEATURE:
<223> OTHER INFORMATION: Synthetic peptide

<400> SEQUENCE: 9

Lys Ser Ala Ser Leu Pro Pro Val Asn Thr Asp Val His Asp Trp Val
1               5                   10                  15

Lys Thr Lys Gly
            20

<210> SEQ ID NO 10
<211> LENGTH: 20
<212> TYPE: PRT
<213> ORGANISM: Artificial sequence
<220> FEATURE:
<223> OTHER INFORMATION: Synthetic peptide

<400> SEQUENCE: 10

Asp Val His Asp Trp Val Lys Thr Lys Gly Ala Trp Asp Lys Gly Tyr
1               5                   10                  15

Lys Gly Gln Gly
            20

<210> SEQ ID NO 11
<211> LENGTH: 20
<212> TYPE: PRT
<213> ORGANISM: Artificial sequence
<220> FEATURE:
<223> OTHER INFORMATION: Synthetic peptide

<400> SEQUENCE: 11

Ala Trp Asp Lys Gly Tyr Lys Gly Gln Gly Lys Val Val Ala Val Ile
1               5                   10                  15

Asp Thr Gly Ile
            20

<210> SEQ ID NO 12
<211> LENGTH: 20
<212> TYPE: PRT
<213> ORGANISM: Artificial sequence

```
<220> FEATURE:
<223> OTHER INFORMATION: Synthetic peptide

<400> SEQUENCE: 12

Lys Val Val Ala Val Ile Asp Thr Gly Ile Asp Pro Ala His Gln Ser
1               5                   10                  15

Met Arg Ile Ser
            20

<210> SEQ ID NO 13
<211> LENGTH: 20
<212> TYPE: PRT
<213> ORGANISM: Artificial sequence
<220> FEATURE:
<223> OTHER INFORMATION: Synthetic peptide

<400> SEQUENCE: 13

Asp Pro Ala His Gln Ser Met Arg Ile Ser Asp Val Ser Thr Ala Lys
1               5                   10                  15

Val Lys Ser Lys
            20

<210> SEQ ID NO 14
<211> LENGTH: 20
<212> TYPE: PRT
<213> ORGANISM: Artificial sequence
<220> FEATURE:
<223> OTHER INFORMATION: Synthetic peptide

<400> SEQUENCE: 14

Asp Val Ser Thr Ala Lys Val Lys Ser Lys Glu Asp Met Leu Ala Arg
1               5                   10                  15

Gln Lys Ala Ala
            20

<210> SEQ ID NO 15
<211> LENGTH: 20
<212> TYPE: PRT
<213> ORGANISM: Artificial sequence
<220> FEATURE:
<223> OTHER INFORMATION: Synthetic peptide

<400> SEQUENCE: 15

Glu Asp Met Leu Ala Arg Gln Lys Ala Ala Gly Ile Asn Tyr Gly Ser
1               5                   10                  15

Trp Ile Asn Asp
            20

<210> SEQ ID NO 16
<211> LENGTH: 20
<212> TYPE: PRT
<213> ORGANISM: Artificial sequence
<220> FEATURE:
<223> OTHER INFORMATION: Synthetic peptide

<400> SEQUENCE: 16

Gly Ile Asn Tyr Gly Ser Trp Ile Asn Asp Lys Val Val Phe Ala His
1               5                   10                  15

Asn Tyr Val Glu
            20

<210> SEQ ID NO 17
<211> LENGTH: 20
<212> TYPE: PRT
```

<213> ORGANISM: Artificial sequence
<220> FEATURE:
<223> OTHER INFORMATION: Synthetic peptide

<400> SEQUENCE: 17

```
Lys Val Val Phe Ala His Asn Tyr Val Glu Asn Ser Asp Asn Ile Lys
1               5                   10                  15

Glu Asn Gln Phe
            20
```

<210> SEQ ID NO 18
<211> LENGTH: 20
<212> TYPE: PRT
<213> ORGANISM: Artificial sequence
<220> FEATURE:
<223> OTHER INFORMATION: Synthetic peptide

<400> SEQUENCE: 18

```
Asn Ser Asp Asn Ile Lys Glu Asn Gln Phe Glu Asp Phe Asp Glu Asp
1               5                   10                  15

Trp Glu Asn Phe
            20
```

<210> SEQ ID NO 19
<211> LENGTH: 20
<212> TYPE: PRT
<213> ORGANISM: Artificial sequence
<220> FEATURE:
<223> OTHER INFORMATION: Synthetic peptide

<400> SEQUENCE: 19

```
Glu Asp Phe Asp Glu Asp Trp Glu Asn Phe Glu Phe Asp Ala Glu Pro
1               5                   10                  15

Lys Ala Ile Lys
            20
```

<210> SEQ ID NO 20
<211> LENGTH: 20
<212> TYPE: PRT
<213> ORGANISM: Artificial sequence
<220> FEATURE:
<223> OTHER INFORMATION: Synthetic peptide

<400> SEQUENCE: 20

```
Glu Phe Asp Ala Glu Pro Lys Ala Ile Lys Lys His Lys Ile Tyr Arg
1               5                   10                  15

Pro Gln Ser Thr
            20
```

<210> SEQ ID NO 21
<211> LENGTH: 20
<212> TYPE: PRT
<213> ORGANISM: Artificial sequence
<220> FEATURE:
<223> OTHER INFORMATION: Synthetic peptide

<400> SEQUENCE: 21

```
Lys His Lys Ile Tyr Arg Pro Gln Ser Thr Gln Ala Pro Lys Glu Thr
1               5                   10                  15

Val Ile Lys Thr
            20
```

<210> SEQ ID NO 22
<211> LENGTH: 20

```
<212> TYPE: PRT
<213> ORGANISM: Artificial sequence
<220> FEATURE:
<223> OTHER INFORMATION: Synthetic peptide

<400> SEQUENCE: 22

Gln Ala Pro Lys Glu Thr Val Ile Lys Thr Glu Glu Thr Asp Gly Ser
1               5                   10                  15

His Asp Ile Asp
            20

<210> SEQ ID NO 23
<211> LENGTH: 20
<212> TYPE: PRT
<213> ORGANISM: Artificial sequence
<220> FEATURE:
<223> OTHER INFORMATION: Synthetic peptide

<400> SEQUENCE: 23

Glu Glu Thr Asp Gly Ser His Asp Ile Asp Trp Thr Gln Thr Asp Asp
1               5                   10                  15

Glu Thr Lys Tyr
            20

<210> SEQ ID NO 24
<211> LENGTH: 20
<212> TYPE: PRT
<213> ORGANISM: Artificial sequence
<220> FEATURE:
<223> OTHER INFORMATION: Synthetic peptide

<400> SEQUENCE: 24

Trp Thr Gln Thr Asp Asp Glu Thr Lys Tyr Glu Ser His Gly Met His
1               5                   10                  15

Val Thr Gly Ile
            20

<210> SEQ ID NO 25
<211> LENGTH: 20
<212> TYPE: PRT
<213> ORGANISM: Artificial sequence
<220> FEATURE:
<223> OTHER INFORMATION: Synthetic peptide

<400> SEQUENCE: 25

Glu Ser His Gly Met His Val Thr Gly Ile Val Ala Gly Asn Ser Lys
1               5                   10                  15

Glu Ala Ala Ala
            20

<210> SEQ ID NO 26
<211> LENGTH: 20
<212> TYPE: PRT
<213> ORGANISM: Artificial sequence
<220> FEATURE:
<223> OTHER INFORMATION: Synthetic peptide

<400> SEQUENCE: 26

Val Ala Gly Asn Ser Lys Glu Ala Ala Ala Thr Gly Glu Arg Phe Leu
1               5                   10                  15

Gly Ile Ala Pro
            20

<210> SEQ ID NO 27
```

```
<211> LENGTH: 20
<212> TYPE: PRT
<213> ORGANISM: Artificial sequence
<220> FEATURE:
<223> OTHER INFORMATION: Synthetic peptide

<400> SEQUENCE: 27

Thr Gly Glu Arg Phe Leu Gly Ile Ala Pro Glu Ala Gln Val Met Phe
1               5                   10                  15

Met Arg Val Phe
            20

<210> SEQ ID NO 28
<211> LENGTH: 20
<212> TYPE: PRT
<213> ORGANISM: Artificial sequence
<220> FEATURE:
<223> OTHER INFORMATION: Synthetic peptide

<400> SEQUENCE: 28

Glu Ala Gln Val Met Phe Met Arg Val Phe Ala Asn Asp Val Met Gly
1               5                   10                  15

Ser Ala Glu Ser
            20

<210> SEQ ID NO 29
<211> LENGTH: 20
<212> TYPE: PRT
<213> ORGANISM: Artificial sequence
<220> FEATURE:
<223> OTHER INFORMATION: Synthetic peptide

<400> SEQUENCE: 29

Ala Asn Asp Val Met Gly Ser Ala Glu Ser Leu Phe Ile Lys Ala Ile
1               5                   10                  15

Glu Asp Ala Val
            20

<210> SEQ ID NO 30
<211> LENGTH: 20
<212> TYPE: PRT
<213> ORGANISM: Artificial sequence
<220> FEATURE:
<223> OTHER INFORMATION: Synthetic peptide

<400> SEQUENCE: 30

Leu Phe Ile Lys Ala Ile Glu Asp Ala Val Ala Leu Gly Ala Asp Val
1               5                   10                  15

Ile Asn Leu Ser
            20

<210> SEQ ID NO 31
<211> LENGTH: 20
<212> TYPE: PRT
<213> ORGANISM: Artificial sequence
<220> FEATURE:
<223> OTHER INFORMATION: Synthetic peptide

<400> SEQUENCE: 31

Ala Leu Gly Ala Asp Val Ile Asn Leu Ser Leu Gly Thr Ala Asn Gly
1               5                   10                  15

Ala Gln Leu Ser
            20
```

```
<210> SEQ ID NO 32
<211> LENGTH: 20
<212> TYPE: PRT
<213> ORGANISM: Artificial sequence
<220> FEATURE:
<223> OTHER INFORMATION: Synthetic peptide

<400> SEQUENCE: 32

Leu Gly Thr Ala Asn Gly Ala Gln Leu Ser Gly Ser Lys Pro Leu Met
1               5                   10                  15

Glu Ala Ile Glu
            20

<210> SEQ ID NO 33
<211> LENGTH: 20
<212> TYPE: PRT
<213> ORGANISM: Artificial sequence
<220> FEATURE:
<223> OTHER INFORMATION: Synthetic peptide

<400> SEQUENCE: 33

Gly Ser Lys Pro Leu Met Glu Ala Ile Glu Lys Ala Lys Lys Ala Gly
1               5                   10                  15

Val Ser Val Val
            20

<210> SEQ ID NO 34
<211> LENGTH: 20
<212> TYPE: PRT
<213> ORGANISM: Artificial sequence
<220> FEATURE:
<223> OTHER INFORMATION: Synthetic peptide

<400> SEQUENCE: 34

Lys Ala Lys Lys Ala Gly Val Ser Val Val Ala Ala Gly Asn Glu
1               5                   10                  15

Arg Val Tyr Gly
            20

<210> SEQ ID NO 35
<211> LENGTH: 20
<212> TYPE: PRT
<213> ORGANISM: Artificial sequence
<220> FEATURE:
<223> OTHER INFORMATION: Synthetic peptide

<400> SEQUENCE: 35

Val Ala Ala Gly Asn Glu Arg Val Tyr Gly Ser Asp His Asp Asp Pro
1               5                   10                  15

Leu Ala Thr Asn
            20

<210> SEQ ID NO 36
<211> LENGTH: 20
<212> TYPE: PRT
<213> ORGANISM: Artificial sequence
<220> FEATURE:
<223> OTHER INFORMATION: Synthetic peptide

<400> SEQUENCE: 36

Ser Asp His Asp Asp Pro Leu Ala Thr Asn Pro Asp Tyr Gly Leu Val
1               5                   10                  15

Gly Ser Pro Ser
            20
```

<210> SEQ ID NO 37
<211> LENGTH: 20
<212> TYPE: PRT
<213> ORGANISM: Artificial sequence
<220> FEATURE:
<223> OTHER INFORMATION: Synthetic peptide

<400> SEQUENCE: 37

```
Pro Asp Tyr Gly Leu Val Gly Ser Pro Ser Thr Gly Arg Thr Pro Thr
1               5                   10                  15

Ser Val Ala Ala
            20
```

<210> SEQ ID NO 38
<211> LENGTH: 20
<212> TYPE: PRT
<213> ORGANISM: Artificial sequence
<220> FEATURE:
<223> OTHER INFORMATION: Synthetic peptide

<400> SEQUENCE: 38

```
Thr Gly Arg Thr Pro Thr Ser Val Ala Ala Ile Asn Ser Lys Trp Val
1               5                   10                  15

Ile Gln Arg Leu
            20
```

<210> SEQ ID NO 39
<211> LENGTH: 20
<212> TYPE: PRT
<213> ORGANISM: Artificial sequence
<220> FEATURE:
<223> OTHER INFORMATION: Synthetic peptide

<400> SEQUENCE: 39

```
Ile Asn Ser Lys Trp Val Ile Gln Arg Leu Met Thr Val Lys Glu Leu
1               5                   10                  15

Glu Asn Arg Ala
            20
```

<210> SEQ ID NO 40
<211> LENGTH: 20
<212> TYPE: PRT
<213> ORGANISM: Artificial sequence
<220> FEATURE:
<223> OTHER INFORMATION: Synthetic peptide

<400> SEQUENCE: 40

```
Met Thr Val Lys Glu Leu Glu Asn Arg Ala Asp Leu Asn His Gly Lys
1               5                   10                  15

Ala Ile Tyr Ser
            20
```

<210> SEQ ID NO 41
<211> LENGTH: 20
<212> TYPE: PRT
<213> ORGANISM: Artificial sequence
<220> FEATURE:
<223> OTHER INFORMATION: Synthetic peptide

<400> SEQUENCE: 41

```
Asp Leu Asn His Gly Lys Ala Ile Tyr Ser Glu Ser Val Asp Phe Lys
1               5                   10                  15

Asp Ile Lys Asp
            20
```

```
<210> SEQ ID NO 42
<211> LENGTH: 20
<212> TYPE: PRT
<213> ORGANISM: Artificial sequence
<220> FEATURE:
<223> OTHER INFORMATION: Synthetic peptide

<400> SEQUENCE: 42

Glu Ser Val Asp Phe Lys Asp Ile Lys Asp Ser Leu Gly Tyr Asp Lys
1               5                   10                  15

Ser His Gln Phe
            20

<210> SEQ ID NO 43
<211> LENGTH: 20
<212> TYPE: PRT
<213> ORGANISM: Artificial sequence
<220> FEATURE:
<223> OTHER INFORMATION: Synthetic peptide

<400> SEQUENCE: 43

Ser Leu Gly Tyr Asp Lys Ser His Gln Phe Ala Tyr Val Lys Glu Ser
1               5                   10                  15

Thr Asp Ala Gly
            20

<210> SEQ ID NO 44
<211> LENGTH: 20
<212> TYPE: PRT
<213> ORGANISM: Artificial sequence
<220> FEATURE:
<223> OTHER INFORMATION: Synthetic peptide

<400> SEQUENCE: 44

Ala Tyr Val Lys Glu Ser Thr Asp Ala Gly Tyr Lys Ala Gln Asp Val
1               5                   10                  15

Lys Gly Lys Ile
            20

<210> SEQ ID NO 45
<211> LENGTH: 20
<212> TYPE: PRT
<213> ORGANISM: Artificial sequence
<220> FEATURE:
<223> OTHER INFORMATION: Synthetic peptide

<400> SEQUENCE: 45

Tyr Lys Ala Gln Asp Val Lys Gly Lys Ile Ala Leu Ile Glu Arg Asp
1               5                   10                  15

Leu Asn Lys Thr
            20

<210> SEQ ID NO 46
<211> LENGTH: 20
<212> TYPE: PRT
<213> ORGANISM: Artificial sequence
<220> FEATURE:
<223> OTHER INFORMATION: Synthetic peptide

<400> SEQUENCE: 46

Ala Leu Ile Glu Arg Asp Leu Asn Lys Thr Tyr Asp Glu Met Ile Ala
1               5                   10                  15

Leu Ala Lys Lys
```

-continued

```
            20

<210> SEQ ID NO 47
<211> LENGTH: 20
<212> TYPE: PRT
<213> ORGANISM: Artificial sequence
<220> FEATURE:
<223> OTHER INFORMATION: Synthetic peptide

<400> SEQUENCE: 47

Tyr Asp Glu Met Ile Ala Leu Ala Lys Lys His Gly Ala Leu Gly Val
1               5                   10                  15

Leu Ile Phe Asn
            20

<210> SEQ ID NO 48
<211> LENGTH: 20
<212> TYPE: PRT
<213> ORGANISM: Artificial sequence
<220> FEATURE:
<223> OTHER INFORMATION: Synthetic peptide

<400> SEQUENCE: 48

His Gly Ala Leu Gly Val Leu Ile Phe Asn Asn Lys Pro Gly Gln Ser
1               5                   10                  15

Asn Arg Ser Met
            20

<210> SEQ ID NO 49
<211> LENGTH: 20
<212> TYPE: PRT
<213> ORGANISM: Artificial sequence
<220> FEATURE:
<223> OTHER INFORMATION: Synthetic peptide

<400> SEQUENCE: 49

Asn Lys Pro Gly Gln Ser Asn Arg Ser Met Arg Leu Thr Ala Asn Gly
1               5                   10                  15

Met Gly Val Pro
            20

<210> SEQ ID NO 50
<211> LENGTH: 20
<212> TYPE: PRT
<213> ORGANISM: Artificial sequence
<220> FEATURE:
<223> OTHER INFORMATION: Synthetic peptide

<400> SEQUENCE: 50

Arg Leu Thr Ala Asn Gly Met Gly Val Pro Ser Ala Phe Ile Ser His
1               5                   10                  15

Glu Phe Gly Lys
            20

<210> SEQ ID NO 51
<211> LENGTH: 20
<212> TYPE: PRT
<213> ORGANISM: Artificial sequence
<220> FEATURE:
<223> OTHER INFORMATION: Synthetic peptide

<400> SEQUENCE: 51

Ser Ala Phe Ile Ser His Glu Phe Gly Lys Ala Met Ser Gln Leu Asn
1               5                   10                  15
```

```
Gly Asn Gly Thr
        20

<210> SEQ ID NO 52
<211> LENGTH: 20
<212> TYPE: PRT
<213> ORGANISM: Artificial sequence
<220> FEATURE:
<223> OTHER INFORMATION: Synthetic peptide

<400> SEQUENCE: 52

Ala Met Ser Gln Leu Asn Gly Asn Gly Thr Gly Ser Leu Glu Phe Asp
1               5                   10                  15

Ser Val Val Ser
        20

<210> SEQ ID NO 53
<211> LENGTH: 20
<212> TYPE: PRT
<213> ORGANISM: Artificial sequence
<220> FEATURE:
<223> OTHER INFORMATION: Synthetic peptide

<400> SEQUENCE: 53

Gly Ser Leu Glu Phe Asp Ser Val Val Ser Lys Ala Pro Ser Gln Lys
1               5                   10                  15

Gly Asn Glu Met
        20

<210> SEQ ID NO 54
<211> LENGTH: 20
<212> TYPE: PRT
<213> ORGANISM: Artificial sequence
<220> FEATURE:
<223> OTHER INFORMATION: Synthetic peptide

<400> SEQUENCE: 54

Lys Ala Pro Ser Gln Lys Gly Asn Glu Met Asn His Phe Ser Asn Trp
1               5                   10                  15

Gly Leu Thr Ser
        20

<210> SEQ ID NO 55
<211> LENGTH: 20
<212> TYPE: PRT
<213> ORGANISM: Artificial sequence
<220> FEATURE:
<223> OTHER INFORMATION: Synthetic peptide

<400> SEQUENCE: 55

Ser Gln Lys Gly Asn Glu Met Asn His Phe Ser Asn Trp Gly Leu Thr
1               5                   10                  15

Ser Asp Gly Tyr
        20

<210> SEQ ID NO 56
<211> LENGTH: 20
<212> TYPE: PRT
<213> ORGANISM: Artificial sequence
<220> FEATURE:
<223> OTHER INFORMATION: Synthetic peptide

<400> SEQUENCE: 56

Leu Arg Arg Asp Leu Asp Ala Ser Arg Glu Ala Lys Lys Gln Val Glu
1               5                   10                  15
```

Lys Ala Leu Glu
            20

<210> SEQ ID NO 57
<211> LENGTH: 29
<212> TYPE: PRT
<213> ORGANISM: Artificial sequence
<220> FEATURE:
<223> OTHER INFORMATION: Synthetic peptide

<400> SEQUENCE: 57

Lys Gln Ala Glu Asp Lys Val Lys Ala Ser Arg Glu Ala Lys Lys Gln
1               5                   10                  15

Val Glu Lys Ala Leu Glu Gln Leu Glu Asp Arg Val Lys
            20                  25

<210> SEQ ID NO 58
<211> LENGTH: 28
<212> TYPE: PRT
<213> ORGANISM: Artificial sequence
<220> FEATURE:
<223> OTHER INFORMATION: Synthetic peptide

<400> SEQUENCE: 58

Gln Ala Glu Asp Lys Val Lys Gln Ser Arg Glu Ala Lys Lys Gln Val
1               5                   10                  15

Glu Lys Ala Leu Lys Gln Leu Glu Asp Lys Val Gln
            20                  25

<210> SEQ ID NO 59
<211> LENGTH: 27
<212> TYPE: PRT
<213> ORGANISM: Artificial sequence
<220> FEATURE:
<223> OTHER INFORMATION: Synthetic peptide

<400> SEQUENCE: 59

Ser Arg Glu Ala Lys Lys Gln Ser Arg Glu Ala Lys Lys Gln Val Glu
1               5                   10                  15

Lys Ala Leu Lys Gln Val Glu Lys Ala Leu Cys
            20                  25

<210> SEQ ID NO 60
<211> LENGTH: 27
<212> TYPE: PRT
<213> ORGANISM: Artificial sequence
<220> FEATURE:
<223> OTHER INFORMATION: Synthetic peptide

<400> SEQUENCE: 60

Ser Arg Glu Ala Lys Lys Gln Ser Arg Glu Ala Lys Lys Gln Val Glu
1               5                   10                  15

Lys Ala Leu Lys Gln Ser Arg Glu Ala Lys Cys
            20                  25

<210> SEQ ID NO 61
<211> LENGTH: 27
<212> TYPE: PRT
<213> ORGANISM: Artificial sequence
<220> FEATURE:
<223> OTHER INFORMATION: Synthetic peptide

<400> SEQUENCE: 61

Ser Arg Glu Ala Lys Lys Gln Val Glu Lys Ala Leu Lys Gln Ser Arg

```
                1               5                      10                      15
Glu Ala Lys Lys Gln Val Glu Lys Ala Leu Cys
                       20                      25

<210> SEQ ID NO 62
<211> LENGTH: 27
<212> TYPE: PRT
<213> ORGANISM: Artificial sequence
<220> FEATURE:
<223> OTHER INFORMATION: Synthetic peptide

<400> SEQUENCE: 62

Ser Arg Glu Ala Lys Lys Gln Val Glu Lys Ala Leu Asp Ala Ser Arg
1               5                      10                      15

Glu Ala Lys Lys Gln Val Glu Lys Ala Leu Cys
                       20                      25

<210> SEQ ID NO 63
<211> LENGTH: 7
<212> TYPE: PRT
<213> ORGANISM: Artificial sequence
<220> FEATURE:
<223> OTHER INFORMATION: Synthetic peptide

<400> SEQUENCE: 63

Met Lys Gln Leu Glu Asp Lys
1               5

<210> SEQ ID NO 64
<211> LENGTH: 7
<212> TYPE: PRT
<213> ORGANISM: Artificial sequence
<220> FEATURE:
<223> OTHER INFORMATION: Synthetic peptide

<400> SEQUENCE: 64

Val Lys Gln Leu Glu Asp Lys
1               5
```

GROUP A STREPTOCOCCUS VACCINE

CROSS REFERENCE TO RELATED APPLICATIONS

This patent application is a divisional of U.S. patent application Ser. No. 15/304,462, now U.S. Pat. No. 10,301,362, which is the U.S. national phase of International Patent Application No. PCT/AU2015/050174, filed Apr. 15, 2015, which claims the benefit of A.U. Patent Application No. 2014901382, filed Apr. 15, 2014, A.U. Patent Application No. 2014903042, filed Aug. 6, 2014, and A.U. Patent Application No. 2014904453, filed Nov. 5, 2014, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: one 18,940 bytes Byte ASCII (Text) filed named "742346_Seq-Listing.txt," created Apr. 25, 2019.

FIELD

This invention relates to prevention and treatment of infectious diseases. More particularly, this invention relates to a vaccine for treating or preventing group A streptococcus and streptococcus-associated diseases and conditions.

BACKGROUND

Vaccines against *Streptococcus pyogenes* (the Lancefield group A streptococcus; GAS) have long been sought due to the debilitating diseases caused by the bacterium, particularly rheumatic fever and rheumatic heart disease. Rheumatic fever is an uncommon disease today in most developed countries but it remains the major cause of acquired heart disease in children, adolescents and young adults in the developing world. In addition, invasive GAS disease is a frequent cause of sepsis in children and adults and has a high-case fatality rate. Further adding to the burden of GAS disease is post-streptococcal glomerulonephritis, which likely contributes to the high rates of end-stage renal failure in many GAS endemic regions. GAS pharyngitis and impetigo are responsible for the greatest absolute number of GAS infections each year. GAS pharyngitis affects approximately 8%-15% of school-aged children per year and GAS impetigo is a very common infection in children prevalence of 10-50%. Not only are severe GAS-associated diseases a problem in developing countries, but even in developed countries particularly virulent GAS strains have emerged that are resistant to standard antibiotic therapies and cause debilitating diseases such as severe necrotizing fasciitis.

An important virulence factor of GAS is M protein, which is strongly anti-phagocytic and binds to serum factor H, destroying C3-convertase and preventing opsonization by C3b. Vaccines have been developed that contain immunogenic peptides from the conserved C-repeat portion of the M protein, such as T and B-cell epitopes from the C-repeat region or the J8 and J14 peptide vaccines that contain single, minimal B cell epitopes from this C-repeat region.

SUMMARY

Surprisingly, the present inventors have discovered that an important factor in J8-peptide induced immunity to group A streptococcus is neutrophil activity. While in vitro opsonisation assays use whole blood as a source of neutrophils and complement, it was not known that neutrophils were required for in vivo protection. Furthermore, opsonisation assays demonstrate relatively modest reductions in CFU (typically less than 10-fold), whereas J8-induced protection in vivo can result in several log order reductions in bacterial bio-burden. More particularly, the inventors now show that neutrophil inhibitors such as SpyCEP which inactivates the neutrophil chemotactic agent interleukin 8 work against J8 in inducing immunity to group A streptococcus.

In a broad form, the invention therefore relates to restoring or enhancing neutrophil activity to thereby assist M protein-induced immunity to group A streptococcus.

An aspect of the invention provides a method of eliciting an immune response to group A streptococcal bacteria in a mammal, said method including the step of administering to the mammal: an M protein fragment, variant or derivative thereof; and an agent that facilitates restoring or enhancing neutrophil activity; to thereby elicit an immune response to group A streptococcal bacteria in the mammal.

Another aspect of the invention provides a method of immunizing a mammal against group A streptococcal bacteria, said method including the step of administering to the mammal: an M protein, fragment, variant or derivative thereof; and an agent that facilitates restoring or enhancing neutrophil activity, to thereby immunize the mammal against group A streptococcal bacteria.

Yet another aspect of the invention provides a method of treating or preventing a group A streptococcal bacterial infection in a mammal, said method including the step of administering to the mammal an M protein fragment, variant or derivative thereof, or an antibody or antibody fragment thereto; and an agent that facilitates restoring or enhancing neutrophil activity; to thereby treat or prevent the group A streptococcal bacterial infection in the mammal.

A further aspect of the invention provides a composition suitable for administration to a mammal, said composition comprising: an M protein fragment, variant or derivative thereof, or an antibody or antibody fragment thereto; and an agent that facilitates restoring or enhancing neutrophil activity.

Related aspects of the invention provide administration of one or more isolated nucleic acids encoding an M protein fragment, variant or derivative thereof and an agent that facilitates restoring or enhancing neutrophil activity or a composition comprising same.

In a particular embodiment the M protein fragment is or comprises a conserved region of the M protein. In one embodiment, the fragment is an immunogenic fragment that comprises, or is contained within a p145 peptide. In a particular embodiment, the immunogenic fragment is within, or comprises, a J8 peptide or variant thereof. On certain embodiments, the variant comprises, consists essentially of consists of an amino acid sequence selected from the group consisting of:
SREAKKQSREAKKQVEKALKQVEKALC (SEQ ID NO:59);
SREAKKQSREAKKQVEKALKQSREAKC (SEQ ID NO:60);
SREAKKQVEKALKQSREAKKQVEKALC (SEQ ID NO:61); and
SREAKKQVEKALDASREAKKQVEKALC (SEQ ID NO:62); or a fragment or variant thereof.

In one broad embodiment, the agent that facilitates restoring or enhancing neutrophil activity is a protein, or a fragment thereof, that normally directly or indirectly inhibits or suppresses neutrophils or neutrophil activity. Suitably, administration of the protein or a fragment thereof elicits an immune response to the protein and/or to group A streptococcus.

Figure 22A:
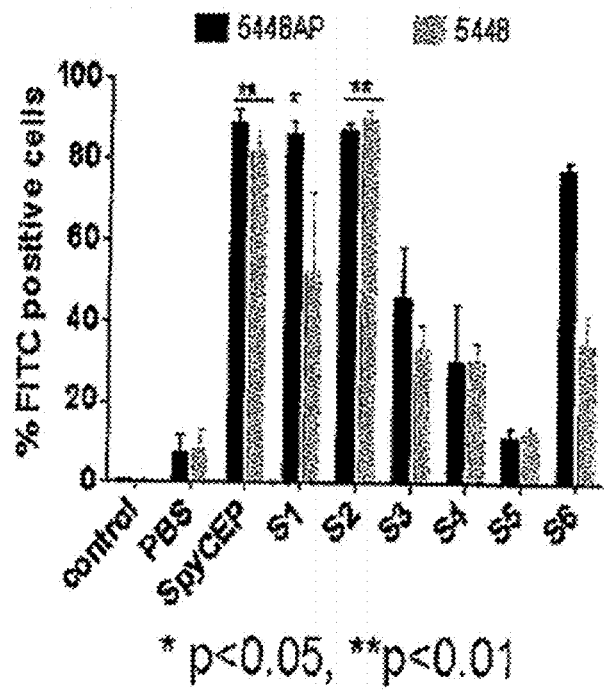
Figure 22B:
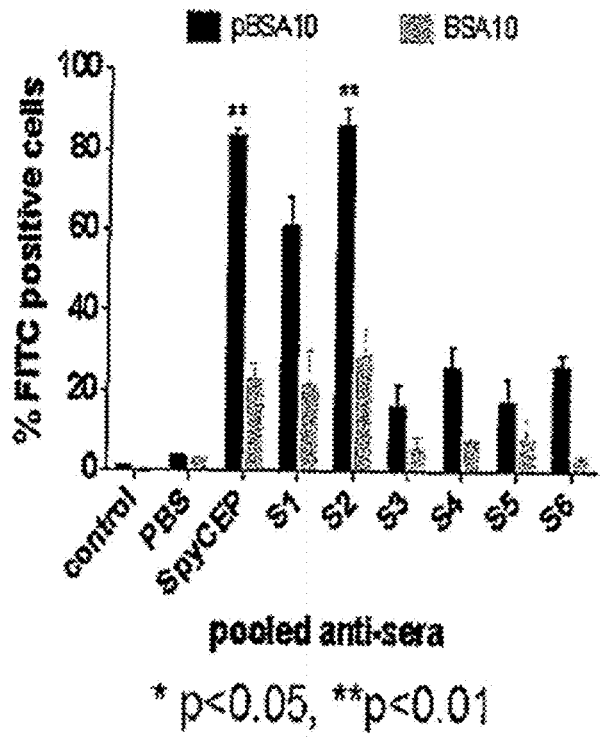
Figure 22C:
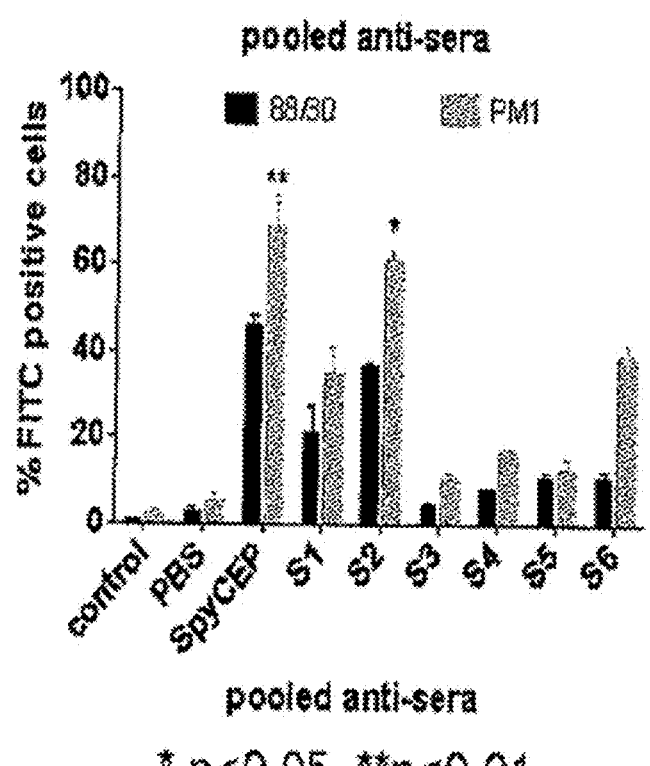

In another broad embodiment, the agent that facilitates restoring or enhancing neutrophil activity is an antibody or antibody fragment which binds a protein, or a fragment thereof, that normally directly or indirectly inhibits or suppresses neutrophils or neutrophil activity.

In a particular embodiment, the protein is SpyCEP, or a fragment thereof.

In a preferred embodiment, the fragment comprises the amino acid sequence NSDNIKENQFEDFDEDWENF (SEQ ID NO:18).

Another further aspect of the invention provides an isolated peptide comprising, consisting essentially of, or consisting of the amino acid sequence selected from the group consisting of NSDNIKENQFEDFDEDWENF (SEQ ID NO:18);

SREAKKQSREAKKQVEKALKQVEKALC (SEQ ID NO:59);

SREAKKQSREAKKQVEKALKQSREAKC (SEQ ID NO:60);

SREAKKQVEKALKQSREAKKQVEKALC (SEQ ID NO:61); and

SREAKKQVEKALDASREAKKQVEKALC (SEQ ID NO:62); or a fragment or variant thereof.

A related aspect provides an isolated nucleic acid encoding the isolated peptide of the aforementioned aspect, a genetic construct comprising the isolated nucleic acid and/or a host cell comprising the genetic construct.

A further related aspect provides an antibody or antibody fragment which binds or is raised against the isolated peptide of the aforementioned aspect.

A still further aspect of the invention provides a composition comprising the isolated peptide, the isolated nucleic acid, the genetic construct, the host cell and/or the antibody or antibody fragment of the previous aspects.

As used herein, the indefinite articles 'a' and 'an' are used here to refer to or encompass singular or plural elements or features and should not be taken as meaning or defining "one" or a "single" element or feature.

Unless the context requires otherwise, the terms "comprise","comprises" and "comprising", or similar terms are intended to mean a non-exclusive inclusion, such that a recited list of elements or features does not include those stated or listed elements solely, but may include other elements or features that are not listed or stated.

By "consisting essentially of" in the context of an amino acid sequence is meant the recited amino acid sequence together with an additional one, two or three amino acids at the N- or C-terminus.

BRIEF DESCRIPTION OF THE DRAWINGS

FIGS. 1A-1C: Protective efficacy of J8-DT/Alum vaccination: (FIG. 1A) M1 throat isolate; (FIG. 1B) 88/30 skin isolate; and (FIG. 1C) BSA10 skin isolate.

FIG. 2: Neutrophils in J8-DT mediated immunity. E: Epidermis; D: Dermis; SC: Sub-cut layer FIGS. 3A-3D: Neutrophil depletion and efficacy of J8-DT vaccination: (FIG. 3A) mouse skin lesion J8-DT PMN; (FIG. 3B) mouse skin lesion J8-DT PMN+; (FIG. 3C) bacterial skin burden; and (FIG. 3D) blood bacteremia.

FIG. 4: Overview of elevated gene expression in the CovR/S mutant GAS an M1T1 isolate.

FIG. 5: Efficacy of J8-DT in protection against 5448AP.

FIG. 6: IL-8 degradation by various GAS strains.

FIG. 7: MIP-2 degradation by various GAS strains.

FIG. 8: KC degradation by various GAS strains.

FIG. 9: Effect of various GAS isolates on chemotactic ability of chemokines.

FIG. 10: Protection against GAS 5448AP strain by immunization with J8-DT-rSpyCEP/Alum.

FIG. 11: Immunogenicity of J8-DT-SpyCEP as measured by antigen-specific IgG production.

FIG. 12: Inhibition of IL-8 degrading activity of SpyCEP by rSpyCEP antisera.

FIGS. 13A-13B: Epitope mapping of overlapping 20mer peptides (10 amino acid overlap) spanning residues 35-587 of SpyCEP (SEQ ID NOS:1-55 in descending order). Bolded peptides are the peptides that were selected by epitope mapping. (FIG. 13A): peptide numbers 1-27=SEQ ID NOS:1-27; (FIG. 13B) peptide numbers 28-55=SEQ ID NOS:28-55.

FIG. 14: Anti-recombinant SpyCEP antisera reactivity with individual peptide epitopes. B-cell epitope mapping of SpyCEP (553 amino acids) was performed using a peptide array. 20-mer peptides overlapping by 10 amino acids as shown in FIGS. 13A-13B were probed with rSpyCEP antisera.

FIG. 15: Identification of six (6) epitopes showing strong reactivity with anti-recombinant SpyCEP antisera. 51=SEQ ID NO:15; S2=SEQ ID NO: 18; S3=SEQ ID NO: 19; S4=SEQ ID NO:24; S5=SEQ ID NO:30; and S6=SEQ ID NO:54.

FIGS. 16A-16B: Immunogenicity and parent peptide recognition by SpyCEP epitope antisera: (FIG. 16A) antigen specific serum; and (FIG. 16B) rSpyCEP specific serum.

FIG. 17: Inhibition of IL-8 degradation by SpyCEP epitope antisera.

FIGS. 18A-18B: Murine a-p145-DT (FIG. 18A) and a-J8-DT (FIG. 18B) titres to self peptides and cross recognition ELISAs.

FIGS. 19A-19D: Murine a-J8iVariant-DT titres to self peptides: (FIG. 19A) anti-J8iV1-DT; (FIG. 19B) anti-J8iV2-DT; (FIG. 19C) antiJ8iV3-DT; and (FIG. 19D) anti-J8iV4-DT.

FIG. 20: Cross Recognition ELISAs.

FIGS. 21A-21C: Identification of immunodominant epitope in recSpyCEP. To identify the immunodominant epitope in recSpyCEP, peptide inhibition ELISA was performed. Cohorts of BALB/c mice (4-6 weeks) were immunized subcutaneously with SpyCEP epitope-DT conjugates or SpyCEP on day 0, 21 and 28. One week after the last boost, the mice were bled via submandibular bleed and antisera were collected. Epitope antisera were incubated with 5 or 0.5 μg/ml concentration of self-peptide and inhibition of self-peptide recognition was assessed (FIG. 21A). The peptide antisera were also incubated with 5 or 0.5 μg/ml concentration of SpyCEP. The sera were then used in an ELISA against immobilised peptides (FIG. 21B). Finally SpyCEP antisera were incubated with 5 or 0.5 μg/ml concentration of each of the peptides (S1-S6) or with recSpyCEP and it's binding to each individual corresponding peptide or SpyCEP was assessed (FIG. 21C). Data for each bar are mean±SEM. Statistical analysis was carried out using a two-way ANOVA with Bonferroni's multiple comparison test to determine significance between the groups. * $p<0.05$ and  $p<0.01$, * $p<0.001$. ns is $p<0.05$.

FIGS. 22A-22C: Binding efficiency of SpyCEP and SpyCEP epitope antisera to various GAS strains. To determine the specificity of recSpyCEP or SpyCEP epitope anti-sera to various GAS strains flow cytometry was carried out. The assay measured the binding of epitope antisera (S1-S6) through FITC conjugated IgG in comparison to SpyCEP anti-sera. Binding of 5448 and its animal passaged derivative (FIG. 22A), BSA10 and its passaged derivative (FIG. 22B) and throat isolate (pM1) and skin isolate (88/30) are shown (FIG. 22C). Data for each bar are mean±SEM. Statistical analysis was carried out using a two-tailed t-test to determine significance in comparison to PBS control. * $p<0.05$, $p<0.01$ and *$p<0.001$.

Figure 23A:
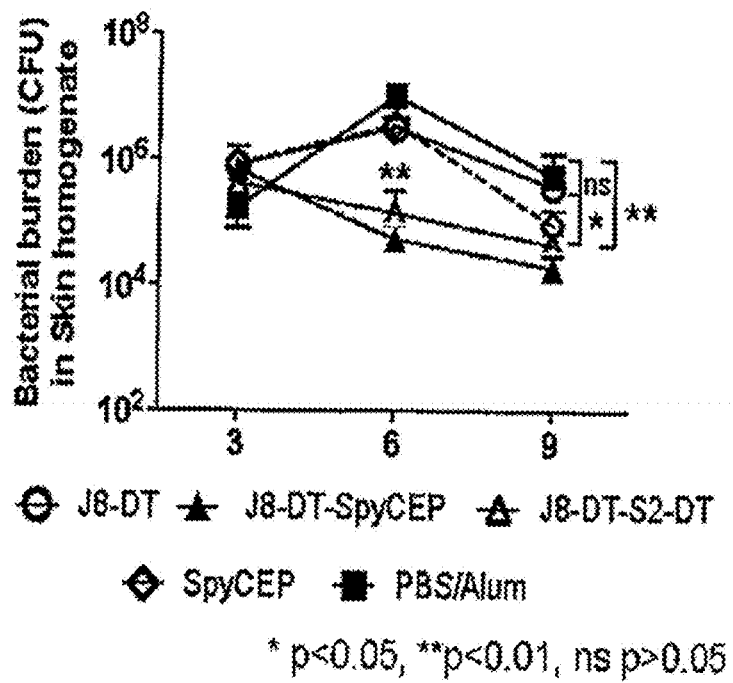
Figure 23B:
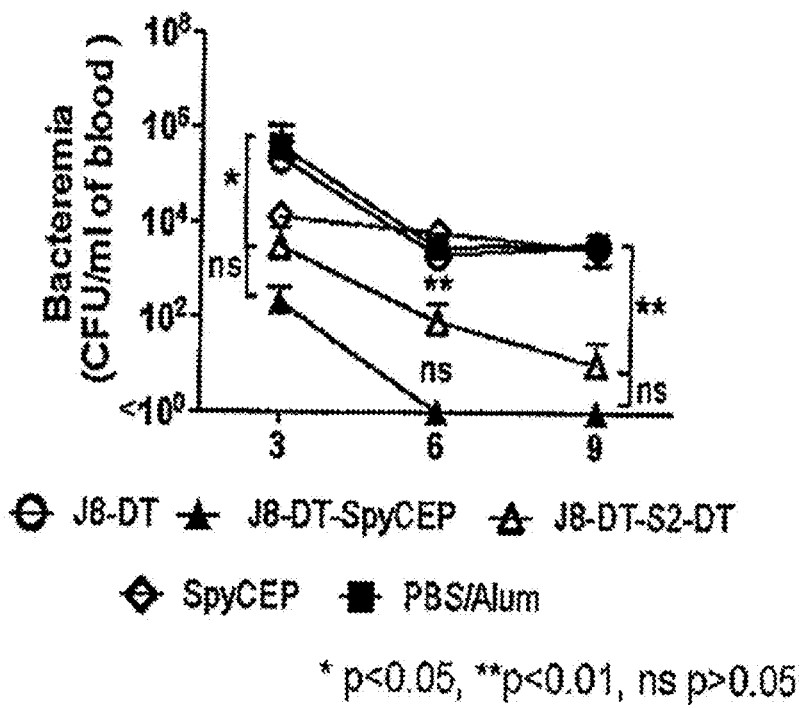

FIGS. 23A-23B: Protective efficacy of J8-DT+S2-DT in protection against GAS. Cohorts of BALB/c mice (4-6 weeks) were immunized subcutaneously with J8-DT, J8-DT+SpyCEP, J8-DT+S2-DT, SpyCEP or PBS formulation on day 0, 21 and 28. Two weeks after the last boost the mice were infected via the skin route of infection with GAS 5448AP (FIGS. 23A-22B). On day 6 post-infection, 5 mice/group were sacrificed and samples were collected to determine GAS bio-burden in the skin (FIG. 23A) and blood (FIG. 23B). Data are representative of two or more independent experiments, and results are shown as mean±SD for 4-5 mice in each group. Two-way ANOVA used to determine significance between vaccinated and control cohort. *$p<0.05$, $p<0.01$, *$p<0.001$. ns is $p<0.05$.

Figure 24A:
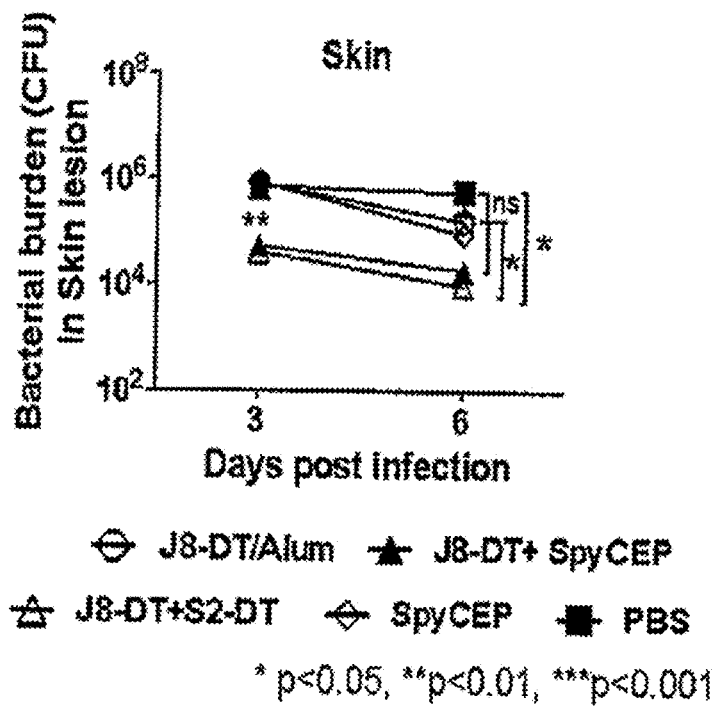
Figure 24B:
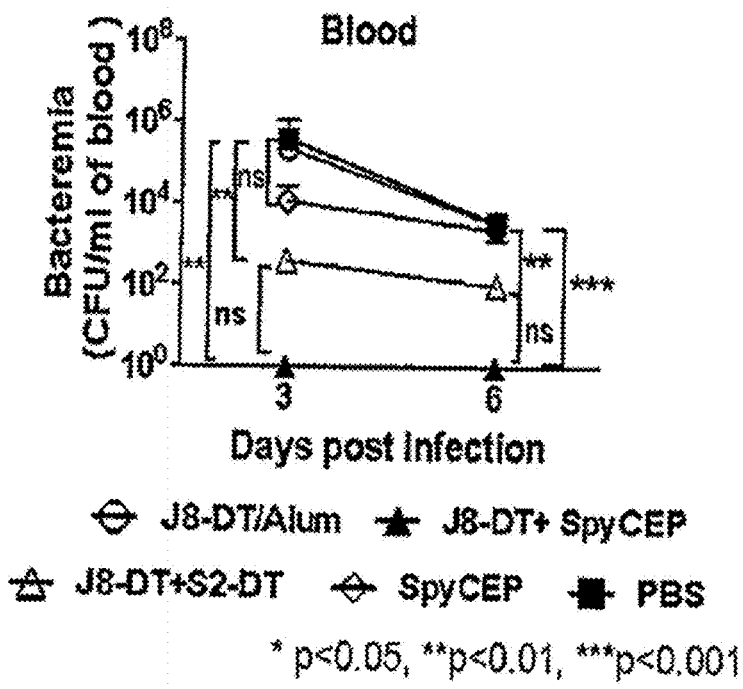

FIGS. 24A-24B: Protective efficacy of J8-DT+S2-DT in protection against GAS. Cohorts of BALB/c mice (4-6 weeks) were immunized subcutaneously with J8-DT, J8-DT+SpyCEP, J8-DT+S2-DT, SpyCEP or PBS formulation on day 0, 21 and 28. Two weeks after the last boost the mice were infected via the skin route of infection with GAS NS22.8 (FIGS. 24A-24B). On days 3 and 6 post-infection, 5 mice/group were sacrificed and samples were collected to determine GAS bio-burden in the skin (FIG. 24A) and blood (FIG. 24B). Results are shown as mean±SD for 4-5 mice in each group. Two-way ANOVA used to determine significance between vaccinated and control cohort. *$p<0.05$, $p<0.01$, *$p<0.001$. ns is $p<0.05$.

DETAILED DESCRIPTION

The present invention is at least partly predicated on the discovery that neutrophil activity is important for successful immunization with J8 peptide against group A streptococci. More particularly, it has been realized that certain proteases of group A streptococci such as SpyCEP exert a deleterious or suppressive effect on neutrophils by proteolytically inactivating the neutrophil chemotactic agent interleukin 8. It is therefore proposed that by immunizing with J8 peptide, or other M protein fragment, and also SpyCEP, an immune response will be elicited to SpyCEP which at least partly reduces the ability of SpyCEP to inactivate interleukin 8 and thereby suppress the neutrophil response. Accordingly, this will synergistically enhance the immunological effect of J8 immunization. In a related embodiment, anti-SpyCEP antibodies may be therapeutically administered to thereby elicit an enhanced immune response to J8 peptide. Furthermore, an immunodominant epitope of SpyCEP has been identified. In a particular form, the invention may be suitable for treating or preventing infections by particularly virulent strains or isolates of Group A streptococci that are resistant to the typical antibiotic treatments used for group A streptococcal infections. These strains or isolates typically cause serious infections of the skin (e.g necrotizing fasciitis) and in some cases may harbour a CovR/SCovR/S mutation.

Accordingly, certain aspects of the invention relate to administering an M protein fragment, variant or derivative thereof and an agent that facilitates restoring or enhancing neutrophil activity to a mammal to thereby elicit an immune response in the mammal.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

By "protein" is meant an amino acid polymer. The amino acids may be natural or non-natural amino acids, D- or L-amino acids as are well understood in the art.

The term "protein" includes and encompasses "peptide", which is typically used to describe a protein having no more than fifty (50) amino acids and "polypeptide", which is typically used to describe a protein having more than fifty (50) amino acids.

A "fragment" is a segment, domain, portion or region of a protein (such as M protein, p145, J14 or J8 or SpyCEP or a SpyCEP peptide or epitope), which constitutes less than 100% of the amino acid sequence of the protein. It will be appreciated that the fragment may be a single fragment or may be repeated alone or with other fragments.

In general, fragments may comprise, consist essentially of or consist of up to 5, 6, 7, 8, 9, 10, 12, 15, 20, 25, 30, 40, 50, 60, 70, 80, 90, 100, 150, 200, 250, 300, 350, 400, 450, 500, 550, 600, 650, 700, 750, 800, 850, 900, 950, 100, 1050, 1100, 1150, 1200, 1250, 1300, 1350, 1400, 1450, 1500, 1550 or 1600 amino acids of the full length protein.

Suitably, the fragment is an immunogenic fragment. In the context of the present invention, the term "immunogenic" as used herein indicates the ability or potential to generate or elicit an immune response, such as to Group A strep or molecular components thereof such as M protein, upon administration of the immunogenic fragment to a mammal. Preferably, the immune response elicited by the immunogenic fragment is protective.

By "elicit an immune response" is meant generate or stimulate the production or activity of one or more elements of the immune system inclusive of the cellular immune system, antibodies and/or the native immune system. Suitably, the one or more elements of the immune system include B lymphocytes, antibodies and neutrophils.

As generally used herein the terms "immunize","vaccinate" and "vaccine" refer to methods and/or compositions that elicit a protective immune response against Group A Strep, whereby subsequent infection by Group A Strep is at least partly prevented or minimized.

As used herein the terms "group A streptococcus", "Group A Streptococci", "Group A Streptococcal","Group A Strep" and the abbreviation "GAS" refer to streptococcal bacteria of Lancefield serogroup A which are gram positive β-hemolytic bacteria of the species *Streptococcus pyogenes*. An important virulence factor of GAS is M protein, which is strongly anti-phagocytic and binds to serum factor H, destroying C3-convertase and preventing opsonization by C3b. These also include virulent "mutants" such as CovR/S or CovRS mutants such as described in Graham et al., 2002, PNAS USA 99 13855, although without limitation thereto.

Diseases and conditions caused by group A streptococci include cellulitis, erysipelas, impetigo, scarlet fever, throat infections such as acute pharyngitis ("strep throat"), bacteremia, toxic shock syndrome, necrotizing fasciitis, acute rheumatic fever and acute glomerulonephritis, although without limitation thereto.

As used herein "neutrophils" or neutrophil granulocytes are cells that form part of the polymorphonuclear cell family (PMNs) together with basophils and eosinophils. Neutrophils are relatively short-lived phagocytic cells formed from bone marrow stem cells and typically constitute 40% to 75% of white blood cells in mammals. As well as being phagocytic neutrophils release soluble anti-microbials (e.g granule proteins) and generate neutrophil extracellular traps. Neutrophils are responsive to molecules such as interleukin-8 (IL-8), C5a, fMLP and leukotriene B4 which promote neutrophil chemotaxis to sites of injury and/or acute inflammation.

As used herein, an "agent that facilitates restoring or enhancing neutrophil activity" is a molecule that directly or indirectly at least partly increases, enhances or restores the production, migration and/or chemotaxis of neutrophils and/or one or more immunological activities of neutrophils. In one embodiment, the agent elicits an immune response to a neutrophil inhibitor. In another embodiment, the agent binds and at least partly inactivates the neutrophil inhibitor. The neutrophil inhibitor may be a molecule derived or originating from Group A Streptococcal bacteria. In one particular form the neutrophil inhibitor is a serine protease, or a fragment thereof, that proteolytically cleaves interleukin 8. In one particular embodiment, the neutrophil inhibitor is SpyCEP or a fragment thereof. SpyCEP is a 170-kDa multidomain serine protease expressed on the surface of the human pathogen *Streptococcus pyogenes*, which plays an important role in infection by catalyzing cleavage and inactivation of the neutrophil chemoattractant interleukin-8. Non-limiting examples of SpyCEP amino acid sequences may be found under accession numbers YP597949.1 and (*S. pyogenes* MGAS10270) and YP596076.1 (*S. pyogenes* MGAS9429). Accordingly, in one particular embodiment the agent that facilitates restoring or enhancing neutrophil activity is SpyCEP or an immunogenic fragment thereof. In another embodiment, the agent that facilitates restoring or enhancing neutrophil activity is an antibody or antibody fragment that binds SpyCEP. Particular embodiments of SpyCEP fragments are set forth in FIGS. 13A-13B (SEQ ID NOS:1-55). A preferred SpyCEP fragment is, or comprises, the amino acid sequence set forth in SEQ ID NO:18 (NSD-NIKENQFEDFDEDWENF). As will be described in more detail hereinafter, An anti-SEQ ID NO:18 peptide antiserum can block the degradation of IL8 as effectively as anti-rSpyCEP antibodies. Thus, it is proposed that SEQ ID NO:18 is, or comprises, the dominant epitope on SpyCEP that can induce functional antibodies.

As used herein an "M protein fragment" is any fragment of a GAS M protein that is immunogenic and/or is capable of being bound by an antibody or antibody fragment. Typically, the fragment is, comprises, or is contained within an amino acid sequence of a C-repeat region of a GAS M protein, or a fragment thereof. Non-limiting examples include p145 which is a 20mer with the amino acid sequence with the amino acid sequence LRRDLDASREAK-KQVEKALE (SEQ ID NO:56). In this regards, fragments of the p145 amino acid sequence may be present in J14 or J8 peptides.

As used herein, a "J14 peptide" may comprise the amino acid sequence KQAEDKVKASREAKKQVEKALEQLEDRVK (SEQ ID NO:57) or a fragment or variant thereof, a peptide with minimal B and T cell epitopes within p145 was identified as a GAS M protein C-region peptide devoid of potentially deleterious T cell autoepitopes, but which contained an opsonic B cell epitope. J14 is a chimeric peptide that contains 14 amino acids from M protein C-region (shown in bold) and is flanked by yeast-derived GCN4 sequences which was necessary to maintain the correct helical folding and conformational structure of the peptide.

As used herein a "J8 peptide" is a peptide which comprises an amino acid sequence at least partly derived from, or corresponding to, a GAS M protein C-region peptide. J8 peptide suitably comprises a conformational B-cell epitope and lacks potentially deleterious T-cell autoepitopes. A preferred J8 peptide amino acid sequence is QAEDKVKQS-REAKKQVEKALKQLEDKVQ (SEQ ID NO:58) or a fragment or variant thereof, wherein the bolded residues correspond to residues 344 to 355 of the GAS M protein. In this embodiment, J8 is a chimeric peptide that further comprises flanking GCN4 DNA-binding protein sequences which assist maintaining the correct helical folding and conformational structure of the J8 peptide.

As used herein, a protein "variant" shares a definable nucleotide or amino acid sequence relationship with a reference amino acid sequence. The reference amino acid sequence may be an amino acid sequence of M protein, SpyCEP or a fragment of these, as hereinbefore described. The "variant" protein may have one or a plurality of amino acids of the reference amino acid sequence deleted or substituted by different amino acids. It is well understood in the art that some amino acids may be substituted or deleted without changing the activity of the immunogenic fragment and/or protein (conservative substitutions). Preferably, protein variants share at least 70% or 75%, preferably at least 80% or 85% or more preferably at least 90%, 91%, 92%, 93%, 94%, 95%, 96%, 97%, 98% or 99% sequence identity with a reference amino acid sequence.

In one particular embodiment, a variant protein or peptide may comprise one or a plurality of lysine residues at an N and/or C-terminus thereof. The plurality of lysine residues (e.g polylysine) may be a linear sequence of lysine residues or may be branched chain sequences of lysine residues. These additional lysine residues may facilitate increased peptide solubility.

Non-limiting examples of J8 peptide variants include:

```
                                                           (SEQ ID NO: 59)
         S R E A K K Q S R E A K K Q V E K A L K Q V E K A L C (SEQ ID NO: 60)
         S R E A K K Q S R E A K K Q V E K A L K Q S R E A K C (SEQ ID NO: 61)
         S R E A K K Q V E K A L K Q S R E A K K Q V E K A L C (SEQ ID NO: 62)
         S R E A K K Q V E K A L D A S R E A K K Q V E K A L C
```

Other variants may be based on heptads such as described in Cooper et al., 1997.

By way of example, if an epitope is known to reside within an α-helix protein structural conformation, then a model peptide can be synthesised to fold to this conformation. We designed a model α-helical coiled coil peptide based on the structure of the GCN4 leucine zipper (O'Shea et al., 1991). The first heptad contains the sequence MKQLEDK (SEQ ID NO:63), which includes several of the features found in a stable coiled coil heptad repeat motif (a-b-c-d-e-f-g)n (Cohen & Parry, 1990). These include large apolar residues in the a and d positions, an acid/base pair (Glu/Lys) at positions e and g (usually favouring interchain ionic interactions), and polar groups in positions b, c, f (consistent with the prediction of Lupas et al. (1991)). The GCN4 peptide also contains a consensus valine in the a position. It has also been noted that when positions a and d are occupied by V and L a coiled coil dimer is favoured (Harbury et al., 1994). A model heptad repeat was derived from these consensus features of the GCN4 leucine zipper peptide: (VKQLEDK; SEQ ID NO:64) with the potential to form a α-helical coiled coil. This peptide became the framework peptide. Overlapping fragments of a conformational epitope under study were embedded within the model coiled coil peptide to give a chimeric peptide. Amino acid substitutions, designed to ensure correct helical coiled coil conformations (Cohen & Parry, 1990) were incorporated into the chimeric peptides whenever an identical residue was found in both the helical model peptide and the epitope sequence. The following substitutions were typically used: position a, V to I; b, K to R; c, Q to N; d, L to A; e, E to Q; f, D to E; g, K to R. All of these replacement residues are commonly found at their respective position in coiled coil proteins (Lupas et al., 1991).

Terms used generally herein to describe sequence relationships between respective proteins and nucleic acids include "comparison window", "sequence identity", "percentage of sequence identity" and "substantial identity". Because respective nucleic acids/proteins may each comprise (1) only one or more portions of a complete nucleic acid/protein sequence that are shared by the nucleic acids/proteins, and (2) one or more portions which are divergent between the nucleic acids/proteins, sequence comparisons are typically performed by comparing sequences over a "comparison window" to identify and compare local regions of sequence similarity. A "comparison window" refers to a conceptual segment of typically 6, 9 or 12 contiguous residues that is compared to a reference sequence. The comparison window may comprise additions or deletions (i.e., gaps) of about 20% or less as compared to the reference sequence for optimal alignment of the respective sequences. Optimal alignment of sequences for aligning a comparison window may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e. resulting in the highest percentage homology over the comparison window) generated by any of the various methods selected. Reference also may be made to the BLAST family of programs as for example disclosed by Altschul et al., 1997, Nucl. Acids Res. 25 3389, which is incorporated herein by reference. A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for windows; available from Hitachi Software engineering Co., Ltd., South San Francisco, Calif., USA).

As used herein, "derivatives" are molecules such as proteins, fragments or variants thereof that have been altered, for example by conjugation or complexing with other chemical moieties, by post-translational modification (e.g. phosphorylation, acetylation and the like), modification of glycosylation (e.g. adding, removing or altering glycosylation), lipidation and/or inclusion of additional amino acid sequences as would be understood in the art. In one particular embodiment, an additional amino acid sequence may comprise one or a plurality of lysine residues at an N and/or C-terminus thereof. The plurality of lysine residues (e.g polylysine) may be a linear sequence of lysine residues or may be branched chain sequences of lysine residues. These additional lysine residues may facilitate increased peptide solubility.

One particular J8 peptide derivative described in Olive et al., 2002, Infect & Immun. 70 2734 is a "lipid core peptide". In one embodiment, a lipid core peptide may comprise a plurality of J8 peptides (e.g four J8 peptides) synthesized directly onto two amino groups of each lysine of a branched polylysine core coupled to a lipophilic anchor.

Additional amino acid sequences may include fusion partner amino acid sequences which create a fusion protein. By way of example, fusion partner amino acid sequences may assist in detection and/or purification of the isolated fusion protein. Non-limiting examples include metal-binding (e.g. polyhistidine) fusion partners, maltose binding protein (MBP), Protein A, glutathione S-transferase (GST), fluorescent protein sequences (e.g. GFP), epitope tags such as myc, FLAG and haemagglutinin tags.

Other derivatives contemplated by the invention include, but are not limited to, modification to side chains, incorporation of unnatural amino acids and/or their derivatives during peptide, or protein synthesis and the use of cross-linkers and other methods which impose conformational constraints on the immunogenic proteins, fragments and variants of the invention.

In this regard, the skilled person is referred to Chapter 15 of CURRENT PROTOCOLS IN PROTEIN SCIENCE, Eds. Coligan et al. (John Wiley & Sons NY 1995-2008) for more extensive methodology relating to chemical modification of proteins.

The isolated immunogenic proteins, fragments and/or derivatives of the present invention may be produced by any means known in the art, including but not limited to, chemical synthesis, recombinant DNA technology and proteolytic cleavage to produce peptide fragments.

Chemical synthesis is inclusive of solid phase and solution phase synthesis. Such methods are well known in the art, although reference is made to examples of chemical synthesis techniques as provided in Chapter 9 of SYNTHETIC VACCINES Ed. Nicholson (Blackwell Scientific Publications) and Chapter 15 of CURRENT PROTOCOLS IN PROTEIN SCIENCE Eds. Coligan et al., (John Wiley & Sons, Inc. NY USA 1995-2008). In this regard, reference is also made to International Publication WO 99/02550 and International Publication WO 97/45444.

Recombinant proteins may be conveniently prepared by a person skilled in the art using standard protocols as for example described in Sambrook et al., MOLECULAR CLONING. A Laboratory Manual (Cold Spring Harbor Press, 1989), in particular Sections 16 and 17; CURRENT PROTOCOLS IN MOLECULAR BIOLOGY Eds. Ausubel et al., (John Wiley & Sons, Inc. NY USA 1995-2008), in particular Chapters 10 and 16; and CURRENT PROTOCOLS IN PROTEIN SCIENCE Eds. Coligan et al., (John Wiley & Sons, Inc. NY USA 1995-2008), in particular Chapters 1, 5 and 6. Typically, recombinant protein preparation includes expression of a nucleic acid encoding the protein in a suitable host cell.

Certain aspects and embodiments relate to administration of one or more nucleic acids encoding an M protein fragment, variant or derivative thereof and an agent that facilitates restoring or enhancing neutrophil activity or a composition comprising same to thereby elicit and immune response to GAS and/or immunize against a GAS infection.

The term "nucleic acid" as used herein designates single- or double-stranded DNA and RNA. DNA includes genomic DNA and cDNA. RNA includes mRNA, RNA, RNAi, siRNA, cRNA and autocatalytic RNA. Nucleic acids may also be DNA-RNA hybrids. A nucleic acid comprises a nucleotide sequence which typically includes nucleotides that comprise an A, G, C, T or U base. However, nucleotide sequences may include other bases such as modified purines (for example inosine, methylinosine and methyladenosine) and modified pyrimidines (for example thiouridine and methylcytosine).

In a preferred form, the one or more isolated nucleic acids encoding an M protein fragment, variant or derivative thereof and an agent that facilitates restoring or enhancing neutrophil activity are in the form of a genetic construct suitable for administration to a mammal such as a human. In a preferred form, the genetic construct is suitable for DNA vaccination of a mammal such as a human.

Suitably, the genetic construct is in the form of, or comprises genetic components of, a plasmid, bacteriophage, a cosmid, a yeast or bacterial artificial chromosome as are well understood in the art. Genetic constructs may also be suitable for maintenance and propagation of the isolated nucleic acid in bacteria or other host cells, for manipulation by recombinant DNA technology.

For the purposes of protein expression, the genetic construct is an expression construct. Suitably, the expression construct comprises the one or more nucleic acids operably linked to one or more additional sequences in an expression vector. An "expression vector" may be either a self-replicating extra-chromosomal vector such as a plasmid, or a vector that integrates into a host genome.

By "operably linked" is meant that said additional nucleotide sequence(s) is/are positioned relative to the nucleic acid of the invention preferably to initiate, regulate or otherwise control transcription.

Regulatory nucleotide sequences will generally be appropriate for the host cell or tissue where expression is required. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The expression construct may also include an additional nucleotide sequence encoding a fusion partner (typically provided by the expression vector) so that the recombinant protein of the invention is expressed as a fusion protein, as hereinbefore described.

It will be understood that the isolated nucleic acids encoding an M protein, fragment, variant or derivative thereof and the agent that facilitates restoring or enhancing neutrophil activity (e.g SpyCEP or an immunogenic fragment thereof) may be administered by way of separate expression constructs or may be present in the same expression construct (eg. a multi-cistronic expression construct).

Suitably, DNA vaccination is by way of one or more plasmid DNA expression constructs. Plasmids typically comprise a viral promoter (such as SV40, RSV or CMV promoters). Intron A may be included to improve mRNA stability and thereby increase protein expression. Plasmids may further include a multiple cloning site, a strong polyadenylation/transcription termination signal, such as bovine growth hormone or rabbit beta-globulin polyadenylation sequences. The plasmid may further comprise Mason-Pfizer monkey virus cis-acting transcriptional elements (MPV-CTE) with or without HIV rev increased envelope expression. Additional modifications that may improve expression include the insertion of enhancer sequences, synthetic introns, adenovirus tripartite leader (TPL) sequences and/or modifications to polyadenylation and/or transcription termination sequences. A non-limiting example of a DNA vaccine plasmid is pVAC which is commercially available from Invivogen.

A useful reference describing DNA vaccinology is DNA Vaccines, Methods and Protocols, Second Edition (Volume 127 of Methods in Molecular Medicine series, Humana Press, 2006).

As hereinbefore described, the invention provides compositions and/or methods of preventing or treating a Group A Strep-associated disease, disorder or condition in a mammal.

As used herein, "treating", "treat" or "treatment" refers to a therapeutic intervention that at least partly ameliorates, eliminates or reduces a symptom or pathological sign of a Group A strep-associated disease, disorder or condition after it has begun to develop. Treatment need not be absolute to be beneficial to the subject. The beneficial effect can be determined using any methods or standards known to the ordinarily skilled artisan.

As used herein, "preventing", "prevent" or "prevention" refers to a course of action initiated prior to infection by, or exposure to, group A strep and/or before the onset of a symptom or pathological sign of a Group A strep-associated disease, disorder or condition, so as to prevent infection and/or reduce the symptom or pathological sign. It is to be understood that such preventing need not be absolute to be beneficial to a subject. A "prophylactic" treatment is a treatment administered to a subject who does not exhibit signs of a group A strep-associated disease, disorder or condition, or exhibits only early signs for the purpose of decreasing the risk of developing a symptom or pathological sign of a Group A strep-associated disease, disorder or condition.

In the context of the present invention, by "group A-strep-associated disease, disorder or condition" is meant any clinical pathology resulting from infection by group A strep and includes cellulitis, erysipelas, impetigo, scarlet fever, throat infections such as acute pharyngitis ("strep throat"), bacteremia, toxic shock syndrome, necrotizing fasciitis, acute rheumatic fever and acute glomerulonephritis, although without limitation thereto.

As hereinbefore described, the treatment and/or immunization methods disclosed herein include administration of the M protein fragment, variant or derivative and the agent that facilitates restoring or enhancing neutrophil activity to a mammal separately, or in combination, to thereby elicit an immune response by the mammal. Alternatively, as hereinbefore described, the treatment and/or immunization methods include administration of one or more isolated nucleic acids encoding an M protein fragment, variant or derivative thereof and an agent that facilitates restoring or enhancing neutrophil activity separately, or in combination, to thereby elicit an immune response by the mammal.

As disclosed herein, other particular aspects and embodiments of the invention relate to use of antibodies or antibody fragments to therapeutically treat GAS infections, such as by targeting SpyCEP at the site of infection (e.g. the skin). This may be performed in combination with M protein fragment immunization and/or administration of anti-M protein fragment antibodies or antibody fragments.

Antibodies and antibody fragments may be polyclonal or monoclonal, native or recombinant. Antibody fragments include Fc, Fab or F(ab)2 fragments and/or may comprise single chain Fv antibodies (scFvs). Such scFvs may be prepared, for example, in accordance with the methods described respectively in U.S. Pat. No. 5,091,513, European Patent No 239,400 or the article by Winter & Milstein, 1991, Nature 349:293. Antibodies may also include multivalent recombinant antibody fragments, such as diabodies, triabodies and/or tetrabodies, comprising a plurality of scFvs, as well as dimerisation-activated demibodies (e.g. WO/2007/062466). By way of example, such antibodies may be prepared in accordance with the methods described in Holliger et al., 1993 Proc Natl Acad Sci USA 90 6444; or in Kipriyanov, 2009 Methods Mol Biol 562 177. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. *Antibodies: A Laboratory Manual*, Cold Spring Harbor, Cold Spring Harbor Laboratory, 1988.

Methods of producing polyclonal antibodies are well known to those skilled in the art. Exemplary protocols which may be used are described for example in Coligan et al., CURRENT PROTOCOLS IN IMMUNOLOGY, supra, and in Harlow & Lane, 1988, supra. In a particular embodiment, anti-SpyCEP polyclonal antibodies may be obtained or purified from human sera from individuals exposed to, or infected by, Group A strep. Alternatively, polyclonal antibodies may be raised against purified or recombinant SpyCEP, or an immunogenic fragment thereof, in production species such as horses and then subsequently purified prior to administration.

Monoclonal antibodies may be produced using the standard method as for example, originally described in an article by Kohler & Milstein, 1975, Nature 256, 495, or by more recent modifications thereof as for example, described in Coligan et al., CURRENT PROTOCOLS IN IMMUNOLOGY, supra by immortalizing spleen or other antibody producing cells derived from a production species which has been inoculated with one or more of the isolated proteins, fragments, variants or derivatives of the invention. Accordingly, monoclonal antibodies may be raised against an M protein fragment, variant or derivative and/or the agent that facilitates restoring or enhancing neutrophil activity (e.g SpyCEP) for use according to the invention. In certain embodiments, the monoclonal antibody or fragment thereof may be in recombinant form. This may be particularly advantageous for "humanizing" the monoclonal antibody or fragment if the monoclonal antibody is initially produced by spleen cells of a non-human mammal.

For embodiments relating to therapeutic antibodies, a preferred M protein fragment may be a p145 peptide.

A preferred fragment of SpyCEP may comprise or consist of the amino acid sequence NSDNIKENQFEDFDEDWENF (SEQ ID NO:18).

In certain aspects and embodiments, the M protein fragment, variant or derivative and the agent that facilitates restoring or enhancing neutrophil activity, inclusive of antibodies or antibody fragments as disclosed herein, may be administered to a mammal separately, or in combination, in the form of a composition.

In a preferred form, the composition comprises an acceptable carrier, diluent or excipient.

By "acceptable carrier, diluent or excipient" is meant a solid or liquid filler, diluent or encapsulating substance that may be safely used in systemic administration. Depending upon the particular route of administration, a variety of carriers, diluent and excipients well known in the art may be used. These may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates, water and pyrogen-free water.

A useful reference describing acceptable carriers, diluents and excipients is Remington's Pharmaceutical Sciences (Mack Publishing Co. N.J. USA, 1991) which is incorporated herein by reference.

Preferably, for the purposes of eliciting an immune response, certain immunological agents may be used in combination with the J8 peptide, fragment, variant or derivative and the agent that facilitates restoring or enhancing neutrophil activity, or with one or more genetic constructs encoding these.

The term "immunological agent" includes within its scope carriers, delivery agents, immunostimulants and/or adjuvants as are well known in the art. As will be understood in the art, immunostimulants and adjuvants refer to or include one or more substances that enhance the immunogenicity and/or efficacy of a composition. Non-limiting examples of suitable immunostimulants and adjuvants include squalane and squalene (or other oils of plant or animal origin); block copolymers; detergents such TWEEN™-80; QUIL™ A, mineral oils such as DRAKEOL or MARCOL, vegetable oils such as peanut oil; *Corynebacterium*-derived adjuvants such as *Corynebacterium parvum; Propionibacterium*-derived adjuvants such as *Propionibacterium acne; Mycobacterium bovis* (Bacille Calmette and Guerin or BCG); *Bordetella pertussis* antigens; tetanus toxoid; diphtheria toxoid; surface active substances such as hexadecylamine, octadecylamine, octadecyl amino acid esters, lysolecithin, dimethyldioctadecylammonium bromide, N,N-dicoctadecyl-N', N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminium phosphate, aluminium hydroxide or alum; interleukins such as interleukin 2 and interleukin 12; monokines such as interleukin 1; tumour necrosis factor; interferons such as gamma interferon; immunostimulatory DNA such as CpG DNA, combinations such as saponin-aluminium hydroxide or QUIL™-A aluminium hydroxide; liposomes; ISCOM™ and ISCOMATRIX™ adjuvant; mycobacterial cell wall extract; synthetic glycopeptides such as muramyl dipeptides or other derivatives; Avridine; Lipid A derivatives; dextran sulfate; DEAE-Dextran alone or with aluminium phosphate; carboxypolymethylene such as CARBOPOL EMA; acrylic copolymer emulsions such as NEOCRYL 640 (e.g. U.S. Pat. No. 5,047,238); water in oil emulsifiers such as MONTANIDE ISA 720; poliovirus, vaccinia or animal poxvirus proteins; or mixtures thereof.

Immunological agents may include carriers such as thyroglobulin; albumins such as human serum albumin; toxins, toxoids or any mutant crossreactive material (CRM) of the toxin from tetanus, diphtheria, pertussis, *Pseudomonas*, *E. coli*, *Staphylococcus*, and *Streptococcus*; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immunogenic protein may be used. For example, a T cell epitope of a bacterial toxin, toxoid or CRM may be used. In this regard, reference may be made to U.S. Pat. No 5,785,973 which is incorporated herein by reference.

Any suitable procedure is contemplated for producing vaccine compositions. Exemplary procedures include, for example, those described in New Generation Vaccines (1997, Levine et al., Marcel Dekker, Inc. New York, Basel, Hong Kong), which is incorporated herein by reference.

In some embodiments, compositions and vaccines may be administered to mammals in the form of attenuated or inactivated bacteria that may be genetically modified to express the J8 peptide, fragment, variant or derivative and/or the agent that facilitates restoring or enhancing neutrophil activity. Non-limiting examples of attenuated bacteria include *Salmonella* species, for example *Salmonella enterica* var. Typhimurium or *Salmonella typhi*. Alternatively, other enteric pathogens such as *Shigella* species or *E. coli* may be used in attenuated form. Attenuated *Salmonella* strains have been constructed by inactivating genes in the aromatic amino acid biosynthetic pathway (Alderton et al., Avian Diseases 35 435), by introducing mutations into two genes in the aromatic amino acid biosynthetic pathway (such as described in U.S. Pat. No. 5,770,214) or in other genes such as htrA (such as described in U.S. Pat. No. 5,980,907) or in genes encoding outer membrane proteins, such as ompR (such as described in U.S. Pat. No. 5,851,519).

Any safe route of administration may be employed, including oral, rectal, parenteral, sublingual, buccal, intravenous, intra-articular, intra-muscular, intra-dermal, subcutaneous, inhalational, intraocular, intraperitoneal, intracerebroventricular, topical, mucosal and transdermal administration, although without limitation thereto.

Dosage forms include tablets, dispersions, suspensions, injections, solutions, syrups, troches, capsules, nasal sprays, suppositories, aerosols, transdermal patches and the like. These dosage forms may also include injecting or implanting controlled releasing devices designed specifically for this purpose or other forms of implants modified to act additionally in this fashion. Controlled release may be effected by coating with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Compositions may be presented as discrete units such as capsules, sachets, functional foods/feeds or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be administered in a manner compatible with the dosage formulation, and in such amount as effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

As generally used herein, the terms "patient", "individual" and "subject" are used in the context of any mammalian recipient of a treatment or composition disclosed herein. Accordingly, the methods and compositions disclosed herein may have medical and/or veterinary applications. In a preferred form, the mammal is a human.

So that the invention may be fully understood and put into practical effect, reference is made to the following non-limiting Examples.

EXAMPLES

Materials and Methods

Animals: BALB/c mice (female, 4-6 weeks old) were sourced from Animal Resource centre (ARC, Perth, Western Australia). All protocols were approved by Griffith University's Animal Ethics Committee in accordance with the National Health and Medical Research Council (NHMRC) of Australia guidelines.

Bacterial strains and culture media: A number of GAS isolates obtained from various sources were utilized in the study. *S. pyogenes* M1 (emm1), 88/30 (emm 97), BSA10 (emm 124) and NS27 (emm 91), NS1 (emm 100) and 90/31 (emm 57) were obtained from Menzies School of Health Research, Darwin, Australia. The strain 5448AP (emm1) was obtained from Prof Mark Walker's (University of Queensland, Brisbane, Australia) lab. All strains were passaged in mice and made streptomycin (200 µg/ml) resistant by continually replating them on increasing concentrations of streptomycin. To prepare challenge inoculum, the GAS strains were grown at 37° C. in liquid medium containing Todd-Hewitt broth (THB; Oxoid, Australia) supplemented with 1% neopeptone (Difco). For bacterial bio-burden determination following infection, the samples were plated on blood agar plates consisting of the liquid medium described above with 2% agar, 200 µg/ml streptomycin and 2% horse blood.

Peptide synthesis and vaccine formulation: Peptide J8 was synthesized and conjugated to DT by Auspep Pty Ltd (Australia) as described elsewhere (Batzloff et al, 2003). The recombinant SpyCEP was expressed and purified by GenScript USA Inc. All peptides were stored lyophilized or in solution at −80° C. Mice were vaccinated with J8-DT or recombinant SpyCEP at a dose of 30 µg/mouse. For vaccination with combined protein-peptide conjugate vaccine, 30 µg of the peptide conjugate J8-DT and 30 µg of recombinant SpyCEP per mouse were mixed and adsorbed on aluminium hydroxide (ALHYDROGEL, alum) in a ratio of 1:1(v/v).

Establishment of a superficial skin infection model: To develop a superficial skin infection model for GAS, inbred female BALB/c, and outbred Swiss mice (4-6 weeks old) were used. Mice were anesthetized with an intraperitoneal (IP) injection (100 µ/10 g mouse) of Ketamine (100 mg/ml stock)/XYLAZIL-20 (20 mg/ml stock)/water in a ratio 1:1:10. The furs from the back haunch of mice were removed using clippers and shaver. The skin was wiped clean with an ethanol swab and then mechanically scarified with the help of a metal file. Following a skin abrasion, the mice were infected with GAS. An inoculum (20 µl) containing known CFU counts of GAS was topically applied on the scarified skin. Once the inoculum has completely absorbed on the skin, a temporary cover was applied on the wounded site and mice were housed in individual cages. In addition to the superficially infected cohorts, a cohort of air sac infected mice was used as a positive control. These mice were infected following the method of Raeder and Boyle (1993). Mice were monitored daily for infected lesions as well as signs of illness as per the approved score sheet. The wounded site was closely monitored to evaluate the status of infection.

Histology sections: On day 3 post-infection the scarified mice (n=3 per group) with or without GAS skin infection were sacrificed. A skin sample of tissue from the infection site was collected and fixed with buffered formalin, and embedded in paraffin for Haematoxylin & eosin (H&E) staining. Five µm thick tissues sections were then sliced and stained with H & E, as well as with Giemsa and Gram stain to visualize the gram-positive organism. Sections were scanned and read at high magnification using ImageScope software. For immunohistochemistry, the samples were frozen in OCT. Histology was also performed at various time-points following neutrophil and macrophage depletion. Positive cells were counted in five areas of scanned slides and were expressed as the average number of positive cells per 10,000 µm$^2$ using ImageJ (National Institute of Health, Bethesda, Md., USA).

Mouse immunization and challenge protocol: BALB/c mice were immunized subcutaneously at the tail base on day 0 with 30 µg of J8-DT, 30 µg of rSpyCEP or 60 µg formulation containing 30 µg of J8-DT and 30 µg of rSpyCEP. All antigen preparations in PBS were formulated in ALHYDROGEL as an adjuvant. Mice were boosted on day 21 and 28. Control mice received adjuvant alone. Two weeks after the final immunization, mice were challenged with GAS using skin route of infection. Post-infection the mice were monitored closely and any mice showing signs of illness (based on score sheet, approved by GU animal ethics committee) were sacrificed.

Sample collection and CFU determination: At defined time-points post-infection (day 3, 6 and & 9) 5 mice from each group were culled. Blood samples were collected via cardiac puncture and skin tissue was excised from the infected lesions at the back haunch of the infected mice. The skin samples were weighed and homogenized in saline. Appropriate dilutions were then plated in replicates on Streptomycin-blood-agar plates to determine bacterial load in the infected lesion. Blood samples were diluted in PBS and appropriate dilutions were plated in replicates on streptomycin-blood-agar plates to determine bacterial load in the blood.

Cell depletion Studies: Macrophages were depleted via IP administration of carrageenan (CGN) as previously described (Goldmann et al, 2004). For depletion of skin macrophages, CGN was injected subcutaneously every 72 hours which resulted in>95% depletion of skin resident macrophages. The dose and time-course for CGN injection was optimized using flow cytometric analysis of spleen cells following labeling with FITC-conjugated anti-mouse Mac-1 and APC conjugated F4/80 (BD Biosciences, New Jersey, USA). To deplete neutrophils, anti-Ly6G mAb (clone 1A8) were used as previously described (Eyles, et al, 2008). The depletion of neutrophils was confirmed by flow cytometric analysis of blood, bone-marrow and spleen cells using CD11b-perCp-cy5.5 and Gr-1-APC mAbs.

Assay of chemokine degradation in vitro: IL-8, MIP-2 and KC degradation was performed and quantified by ELISA using the Quantikine kit (R & D systems, Minneapolis, Minn., USA) as described previously (Hidalgo-Grass et al, 2004). Using this method, the amounts of undegraded chemokines (IL-8, MIP-2 and KC) post incubation with GAS culture supernatants (S/N) were measured. Briefly, to collect culture S/N, various GAS strains were grown to mid-log phase ($OD_{600}$ 0.5), re-inoculated into fresh THB and grown overnight at 37° C. Cell-free GAS culture S/Ns from each strain were then incubated at 37° C. with a known concentration of recombinant chemokine (IL-8, MIP-2 and KC). Samples were collected at 2, 4, 8 or 24 h and the amount of undegraded chemokine determined by ELISA (R & D Systems) as described above.

Neutrophil isolation and transwell migration assays: Neutrophils were isolated from mouse bone-marrow using neutrophil isolation kit (Miltenyi Biotech, Germany). Neutrophils ($2.5 \times 10^5$ in 100 µl media) were added to the upper chamber of the transwell system (Costar 24-well transwell, Corning N.Y.), which was then placed in the lower chamber containing media alone or intact or degraded chemokines. As a positive control, wells containing known concentration of each recombinant chemokine were also used. Following 2 h of incubation at 37° C., the cells were collected from both upper and lower chambers and the number of viable neutrophils transmigrated were determined using trypan blue exclusion. Percentage of migrating neutrophils was calculated by dividing the number of migrating neutrophils by the total number of neutrophils present.

SpyCEP neutralization assays: To assess the SpyCEP neutralizing ability of rSpyCEP antisera, hyper-immune serum to rSpyCEP was raised in BALB/C mice. A panel of GAS strains including 90/31, BSA10 and 5448AP were grown to stationary phase. The cell-free GAS culture supernatants were co-incubated with recombinant chemokines and either 50% normal or anti-SpyCEP serum for 16 h at 37° C. Uncleaved IL-8 was measured using a Quantikine ELISA kit (R & D Systems).

SpyCEP Epitope mapping: A peptide array encompassing 553 amino acids from the N-terminal region of SpyCEP was synthesized at GenScript (Genscript USA Inc). In total 55 peptides (SEQ ID NOS:1-55), each 20-mer overlapping by 10 were blotted on to the membrane. Following an ELISA protocol, the membrane was probed with antisera from mice immunized 3 times with 30 ug/dose of rSpyCEP/Alum preparation. Six peptides that were recognized most strongly with SpyCEP antisera were taken for further studies (SEQ ID NOS: 15, 18, 19, 24, 30 and 54).

Peptide synthesis and vaccine formulation: Six peptides (20-mer each) identified by epitope mapping (as discussed above) were synthesized at GenScript either as a free peptide or with an additional Cysteine residue at the C-terminus. The peptides with C-terminus were then conjugated to DT and were used in mice for in vivo immunogenicity studies. All peptides were stored lyophilized or in solution at −20° C. Mice were vaccinated 3 times with rSpyCEP or SpyCEP peptide (S1-S6)-DT conjugates at a dose of 30 µg/mouse.

Determination of immunogenicity of individual peptides: Serum samples were collected before and after each boost to determine antibody titers to the immunizing peptides as well as to the parent protein (rSpyCEP). To determine peptide specific IgG titers, plates were coated with 5 ug/ml of each of the six peptides (S1-S6). ELISA was carried out using 2-fold serial dilutions of antiserum raised against each peptide. To determine SpyCEP peptide recognition by rSpyCEP, two-fold serial dilution of rSpyCEP antiserum was used. Finally, to determine parent peptide recognition of peptide anti-sera, the plates were coated with rSpyCEP and peptide antisera was used to assess its binding/recognition of rSpyCEP.

Assay for IL-8 protection in vitro: To assess the ability of peptide antisera in inhibiting IL-8 degradation, an in vitro IL-8 protection assay was performed. GAS culture supernatants (S/N) were incubated with a known concentration of recombinant IL-8 and 1:2 dilution of peptide antisera (S1-S6). The amount of undegraded IL-8 in the reaction mixture was quantified by ELISA using the Quantikine kit (R & D systems, Minneapolis, Minn., USA) as described previously (Hidalgo-Grass et al, 2004). Briefly, to collect culture S/N, various GAS strains were grown to mid-log phase ($OD_{600}$ 0.5), re-inoculated into fresh THB and grown overnight at 37° C. Cell-free GAS culture S/Ns from each strain were then incubated at 37° C. with a known concentration of recombinant chemokine (IL-8) and with or without antisera from each peptide. Samples were collected post 16 h of incubation and the amount of undegraded chemokine determined by ELISA (R & D Systems) as described above.

Peptide inhibition ELISA: For the peptide inhibition ELISA assays, the microtiter plates were coated with 100 µl of peptide S1 to S6 or recSpyCEP at a final concentration of 5 µg/ml in 75 mM sodium carbonate buffer, pH 9.6, at 4° C. overnight. Plates were washed with buffer (PBS with 0.05% TWEEN 20, pH 7.2) and blocked for 90 min at 37° C. with buffer supplemented with 5% skim milk (blocking buffer). Anti-peptide or recSpyCEP sera were pre-incubated with 5 or 2.5 µg/ml of each of the self-peptide or recSpyCEP for 30 min at 37° C. Test antisera were thereafter added to the blocked plates and incubated for 90 min at 37° C. The plates were washed four times and HRP-conjugated goat anti-mouse-IgG (Biorad, Australia) was added and incubated for another 90 min at 37° C. After additional washing, the plates were developed as above and $OD_{450}$ measured.

Flow cytometry assay: The binding of the recSpyCEP or SpyCEP epitope antibodies to GAS cell surface was analysed by flow cytometry. The bacteria were grown in THB with 1% neopeptone overnight and washed in PBS. Thereafter, bacteria ($1 \times 10^7$ colony forming units; cfu) were pre-incubated with 100 µl of Fc blocker for 15 min at RT to block the non-specific binding sites. This was followed by addition of the peptide antiserum at a dilution of 1 in 20. After 1 h incubation at RT, the bacteria were washed twice in PBS followed by incubation with a FITC-conjugated anti-mouse IgG (diluted 1/50 in PBS with 2% BSA). Finally, the bacteria were washed and incubated in 1% formaldehyde (in PBS) for 15 min at RT. The samples were analysed in a CyAn ADP Analyzer (Beckman Coulter, Inc.) The FITC-conjugated anti-mouse IgG was added separately as a negative control for each strain analyzed and in addition, a non-specific mouse IgG was included as a control.

Challenge model for assessing vaccine efficacy: Inbred female BALB/c mice (4-6 weeks old) were anesthetized with an intraperitoneal (IP) injection (100 µl/10 g mouse) of Ketamine (100 mg/ml stock)/XYLAZIL-20 (20 mg/ml stock)/water in a ratio 1:1:10. The fur from the nape of the neck of mice was removed using clippers and a shaver. Following superficial scarification of skin, an inoculum (20 µl ) of GAS containing $1 \times 10^6$ CFU counts was topically applied. Once the inoculum had completely absorbed on the skin, a temporary cover was applied on the wounded site and mice were housed in individual cages. Mice were fed on streptomycin (200 µg/ml) water 24 h prior to infection and remained on that throughout the course of study. Mice were monitored daily for infected lesions as well as signs of illness as per the score sheet approved by Griffith University IBC. The wounded site was closely monitored to evaluate the status of infection.

Organ collection and CFU determination: At various time-points post-infection (day 3, 6 and & 9) a defined number of mice from each group were sacrificed. Blood samples were collected via cardiac puncture, spleens were removed and the skin biopsy samples from the infected lesion at the nape of the neck were obtained. The skin and spleen samples were homogenized and appropriate dilutions were then plated in replicates on streptomycin-blood-agar plates. Post-infection, the mice were monitored closely, and any mice showing signs of illness (based on a score sheet) were sacrificed.

Results

Figure 1B:
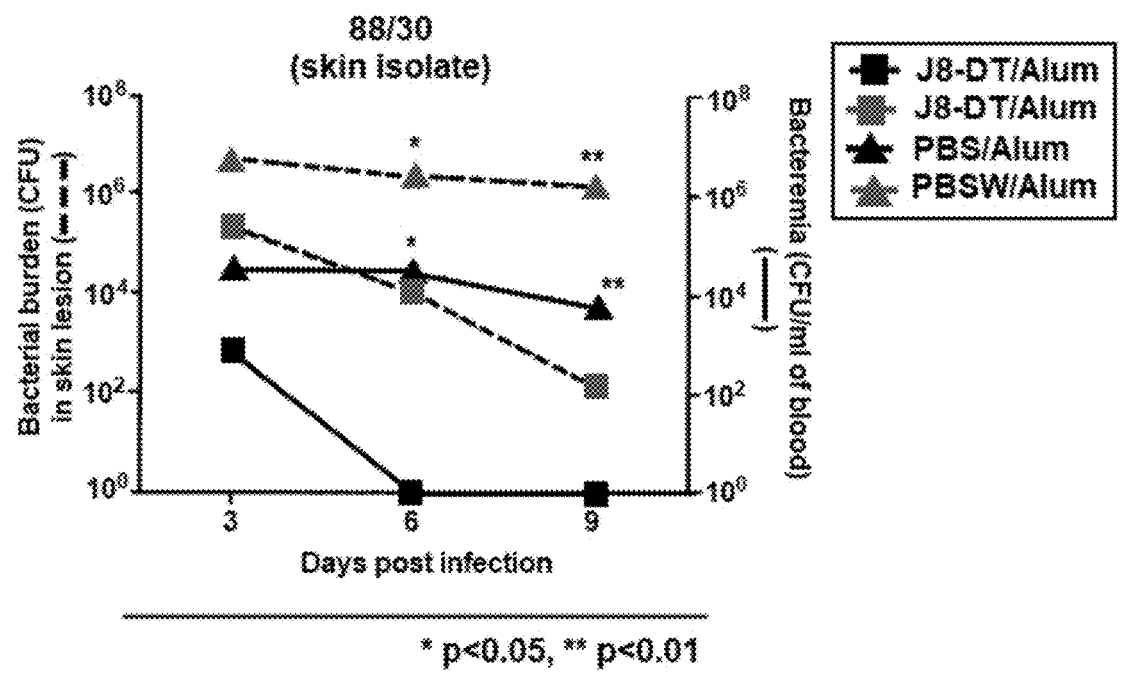
Figure 1C:
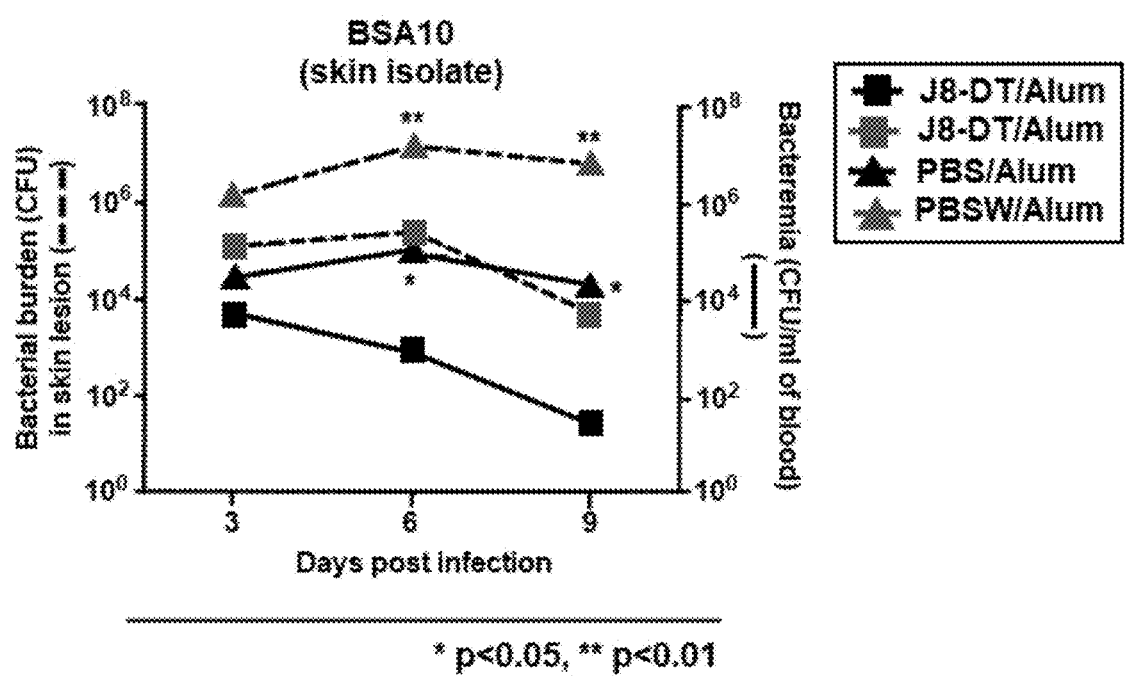
Figure 2:
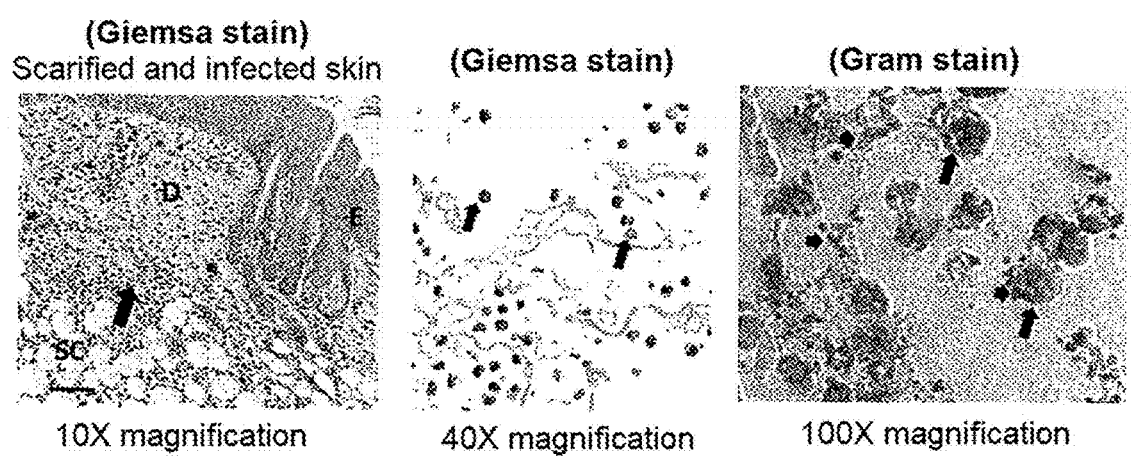
Figure 3A:
Figure 3B:
Figure 3C:
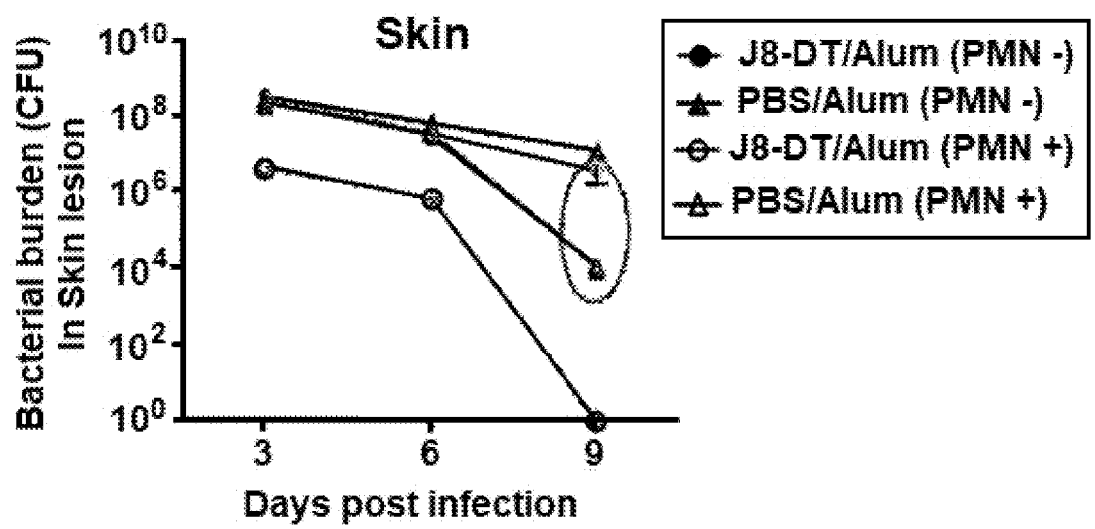
Figure 3D:
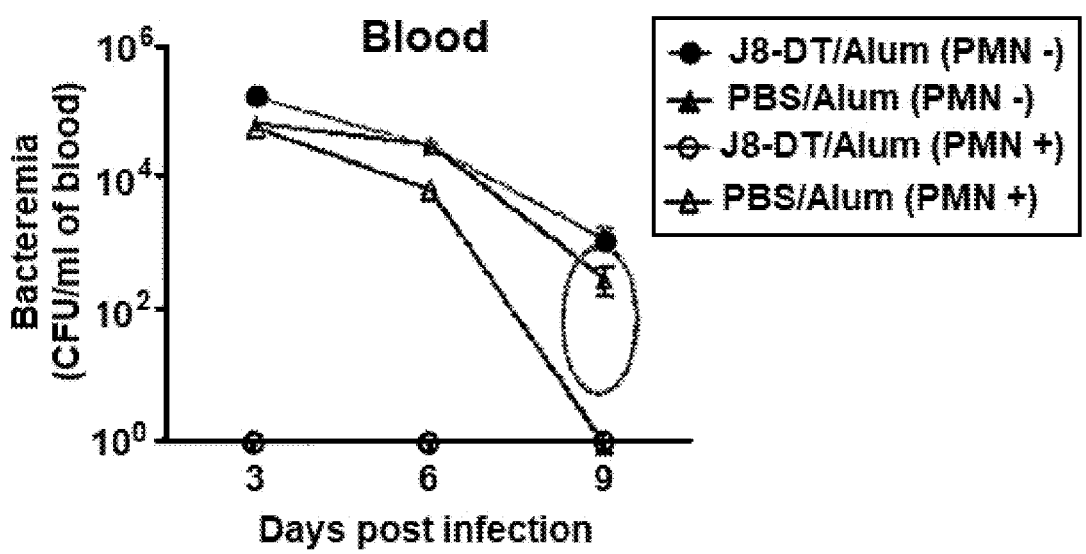

In FIGS. 1A-1C, the protective efficacy of J8-DT/Alum vaccination is shown by comparing different GAS strains M1 (a throat isolate) and skin isolates 88/30 and BSA10. J8-DT/Alum vaccination was less effective for both of the skin isolates compared to M1. Associated with the effectiveness of J8 immunization is the presence of neutrophils (PMN) in the skin of GAS infected mice, as shown in FIG. 2.

Accordingly, experiments were undertaken to measure the effect of neutrophil depletion upon responses to J8-DT/Alum, the results of which are shown in FIGS. 3A-3D. Neutrophil depletion had a deleterious effect on the efficacy of J8-DT/Alum vaccination.

Figure 4:
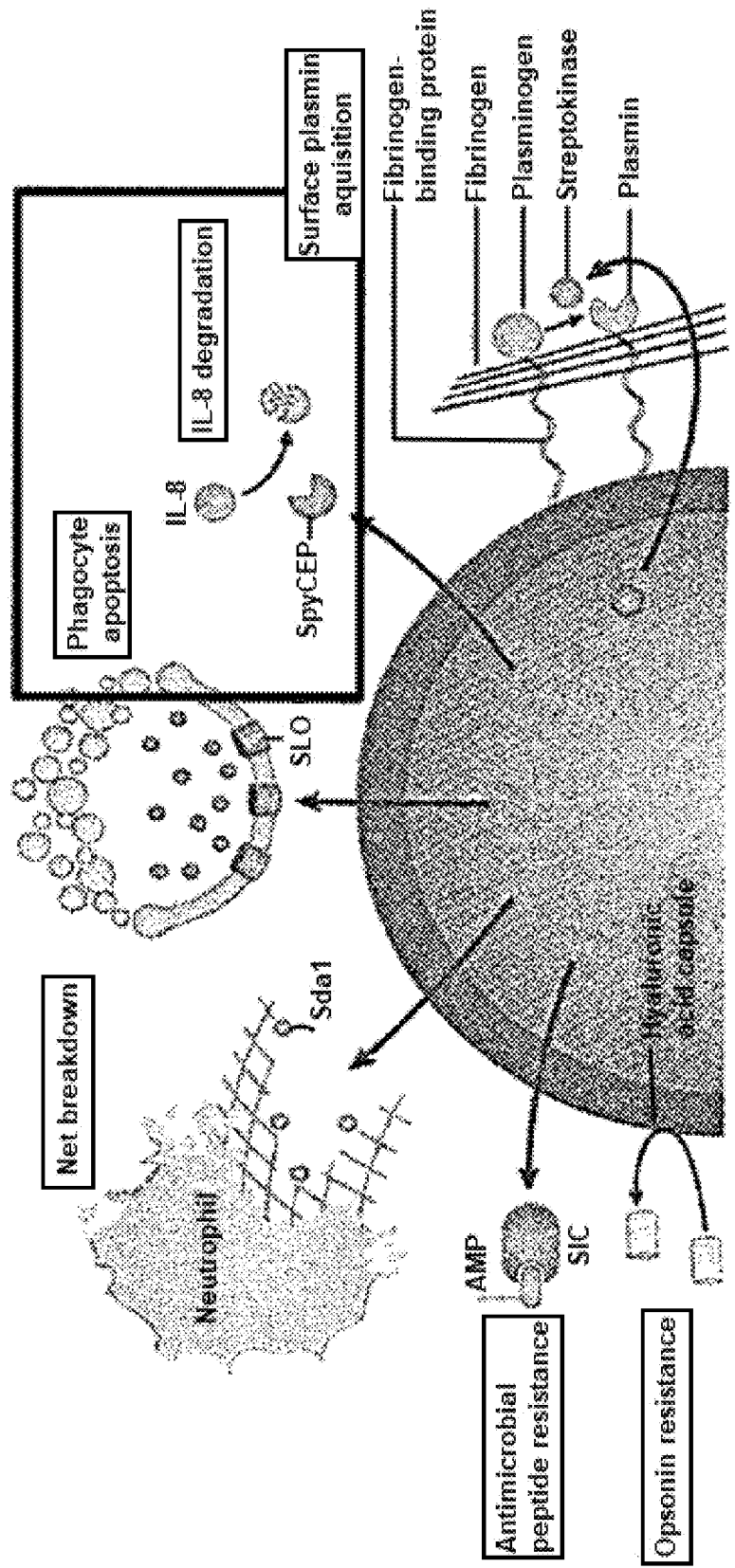
Figure 5:
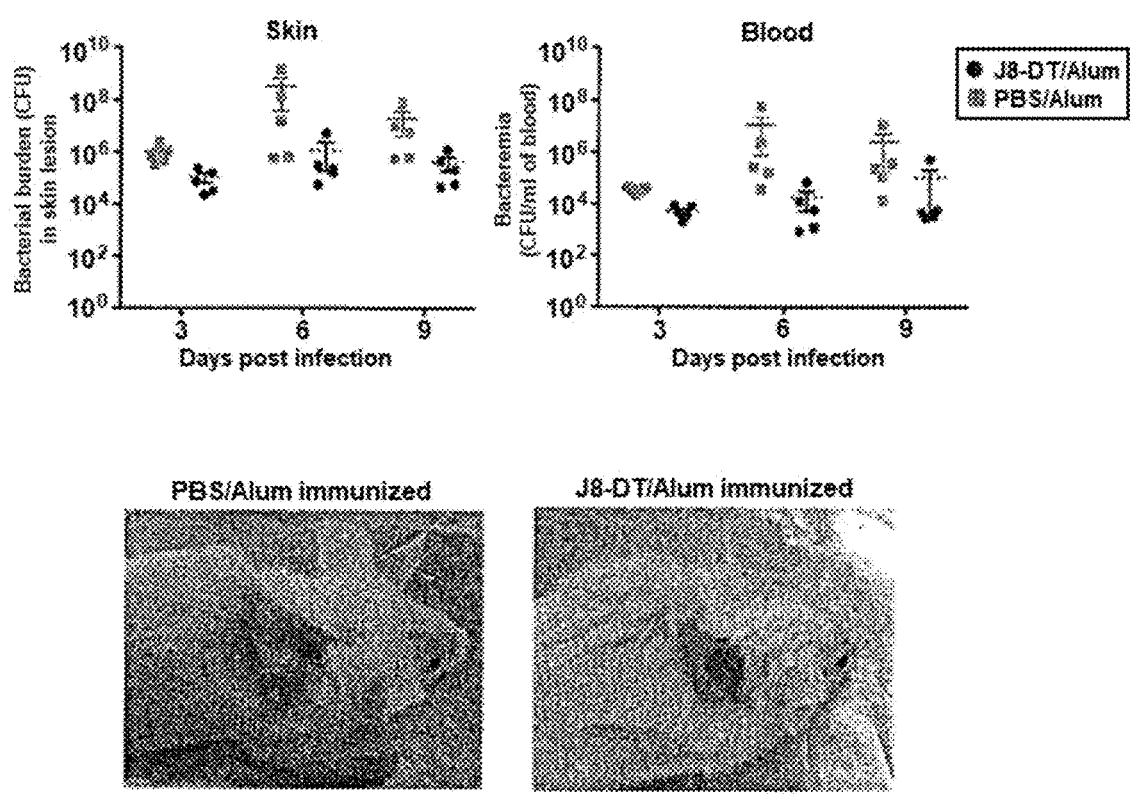
Figure 6:
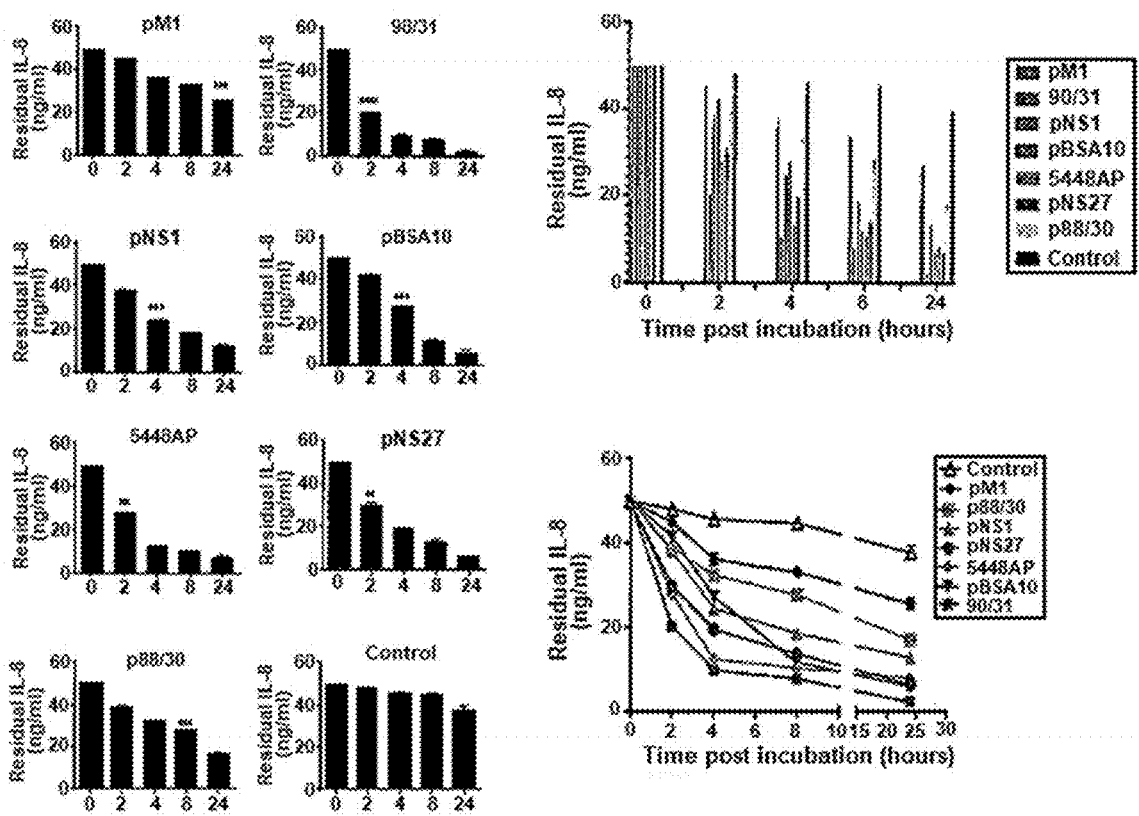
Figure 7:
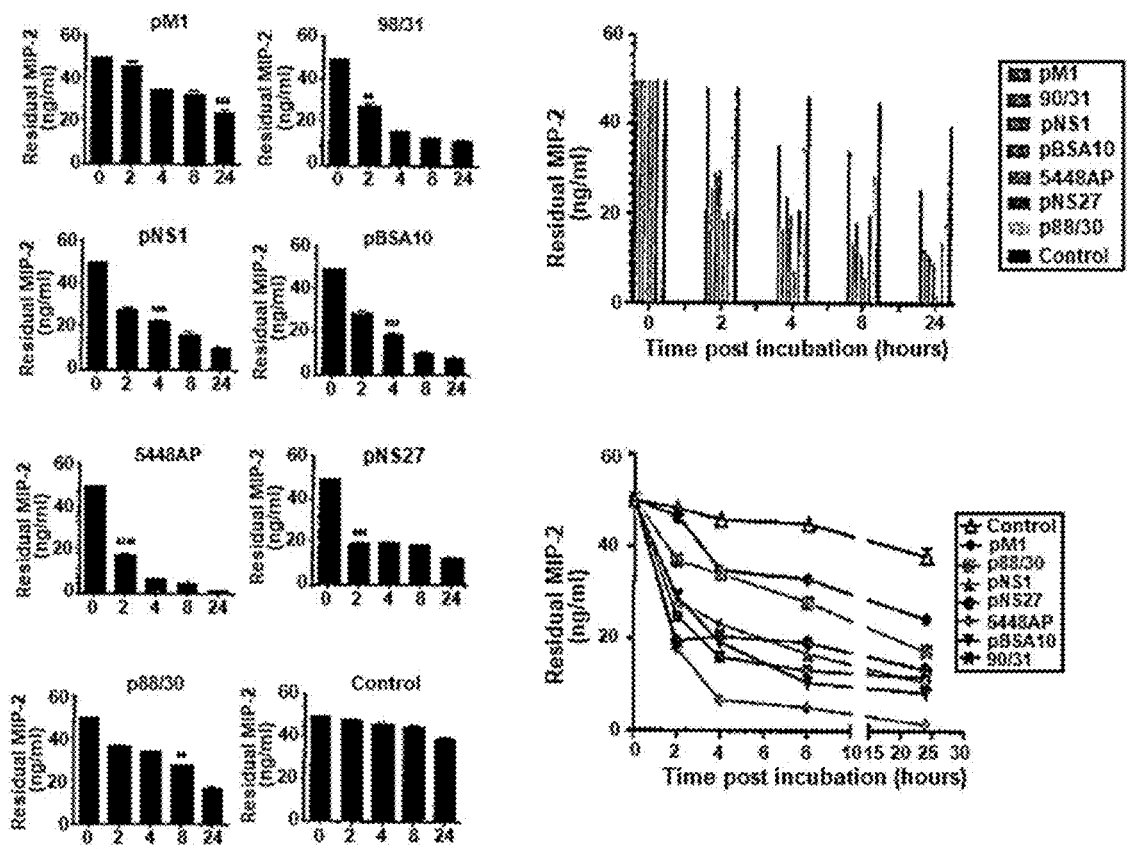
Figure 8:
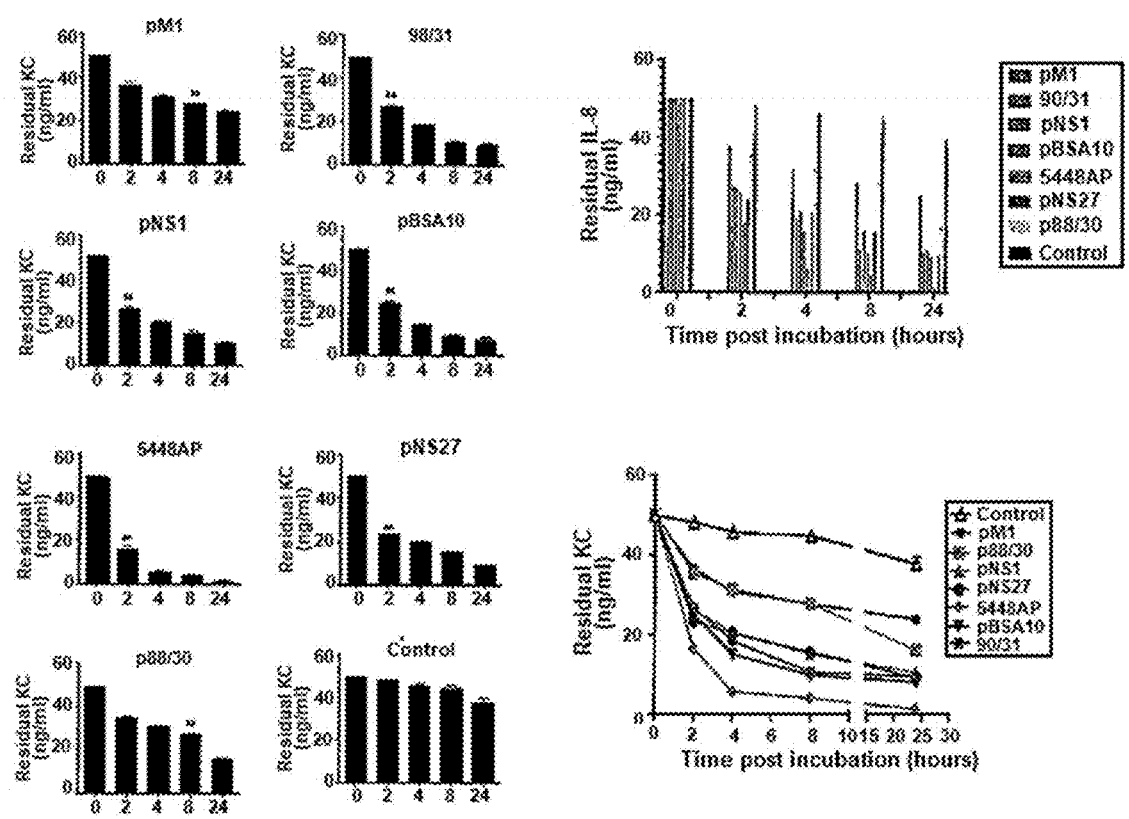

The data in FIGS. 1A-3D suggested that neutrophils may play a role in determining the efficacy of J8 immunization against GAS infection. FIG. 4 provides an overview of the bacterial genes that are expressed upregulated in GAS isolates such as 5448AP (M1T1 isolate) that have a CovR/S mutation. As shown in FIG. 5, the efficacy of J8-DT/Alum protection against GAS isolate 5448AP was relatively poor. Given that neutrophils appear to assist immune responses to J8 peptide, a candidate bacterial gene that is highly expressed in GAS isolate 5448AP was SpyCEP, a 70 kD serine protease that cleaves and inactivates the neutrophil chemoattractant interleukin 8 (see FIG. 4). FIG. 6 shows the results of experiments where 5448AP displayed particularly strong IL-8 degradation. The 5448AP isolate also displayed strong degrading activity toward the murine functional homologues of IL-8: CXCL1/MIP-2 (FIG. 7) and CXCL1/KC (FIG. 8). Functionally, this degradation correlated with an inhibition neutrophil chemotaxis as shown in FIG. 9.

Figure 10:
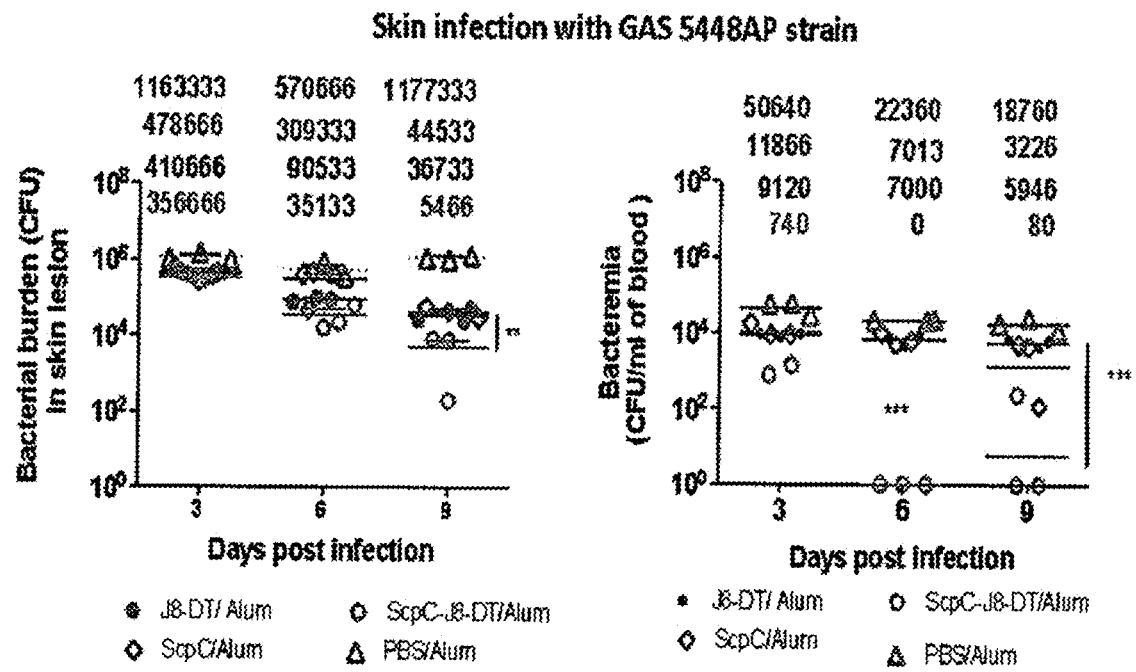
Figure 11:
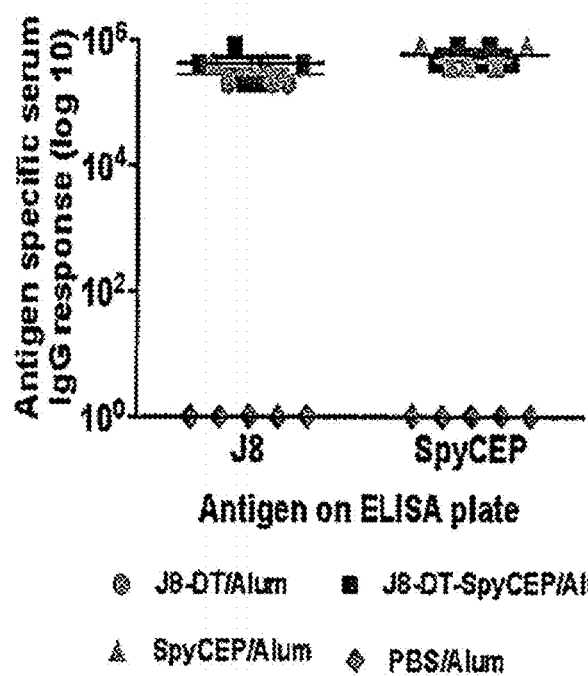
Figure 12:
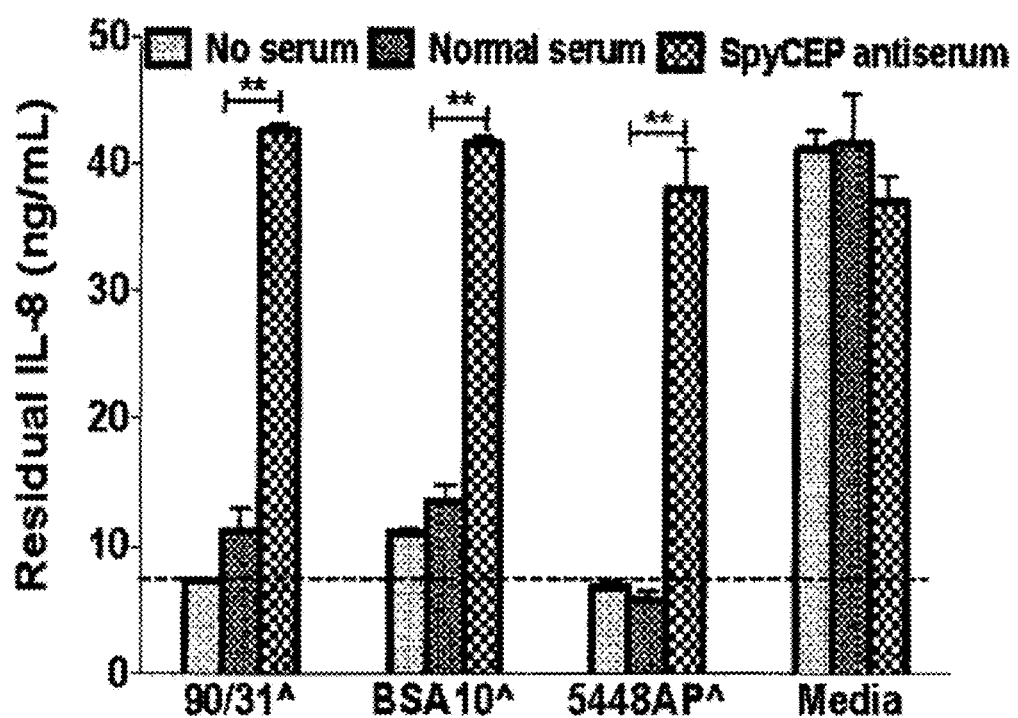

The data in FIGS. 1A-9 suggested that SpyCEP, a serine protease, highly expressed by CovR/SCovR/S mutant GAS bacteria that negatively regulates IL-8 through proteolytic degradation, thereby inhibiting or suppressing neutrophil chemotaxis. Experiments were therefore undertaken to determine whether targeting SpyCEP would improve, restore or augment immune response to J8 peptide. Results shown in FIG. 10 indicated that immunization with J8-DT-recombinant SpyCEP/Alum was far more effective than immunization with J8-DTpeptide-conjugate or recombinant SpyCEP alone, the combination of J8 peptide and recombinant SpyCEP acting synergistically to protect against infection by 5448AP GAS bacteria. Further to this, FIG. 11 shows that immunization with J8-DT-rSpyCEP results in a much stronger IgG antibody response than J8-DT or SpyCEP alone. These data raised the possibility that antibodies to SpyCEP may be useful therapeutic agents that can be administered directly to a site of GAS infection (the skin) to thereby treat the infection. As shown in FIG. 12, anti-SpyCEP antibodies (in the form antisera from mice immunized with recombinant SpyCEP) inhibited the IL-8 degrading activity of SpyCEP.

Figures 14, 15:
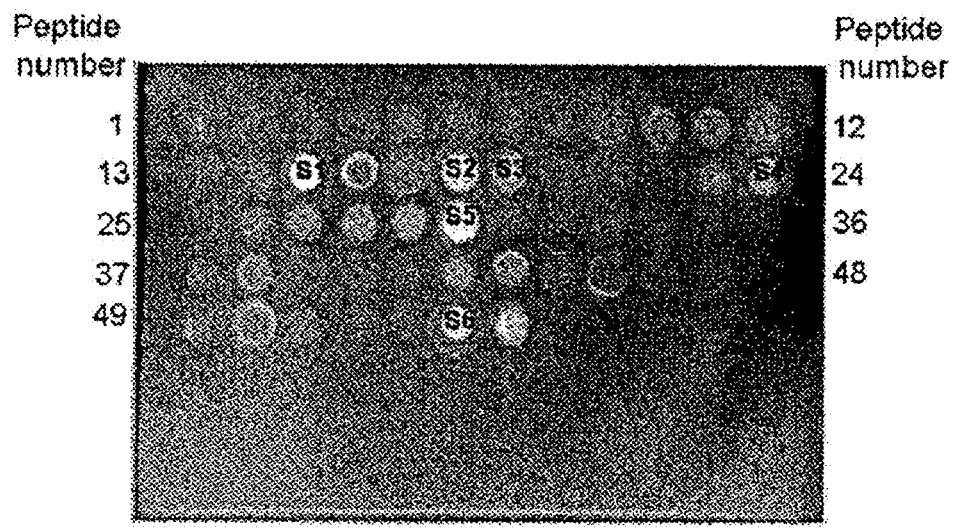
Figure 16A:
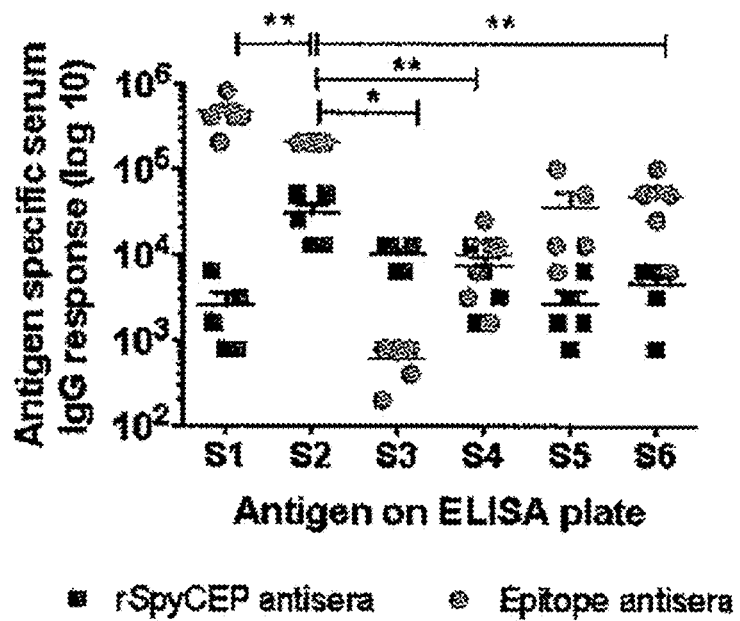
Figure 16B:
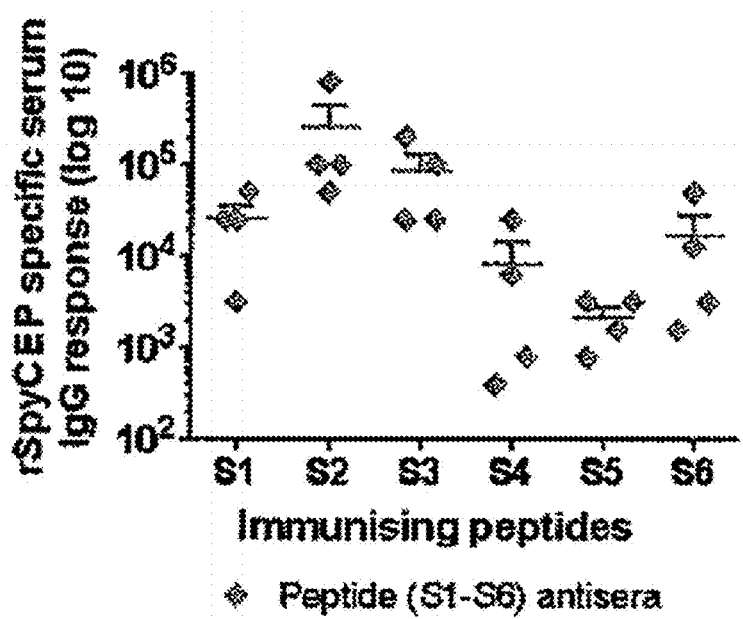
Figure 17:
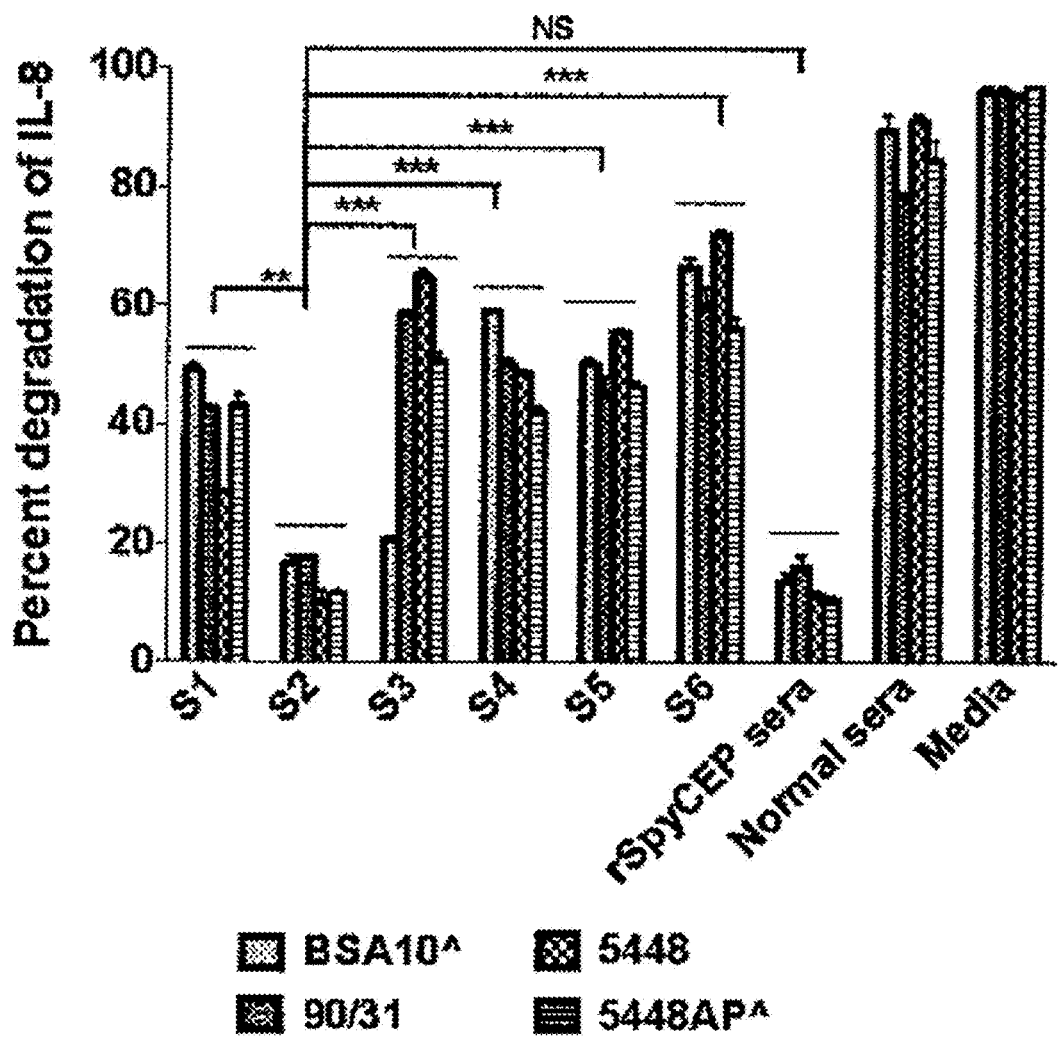

We made a series of overlapping 20mer peptides (peptide array on nitrocellulose membrane) from residues 35-587 of SpyCEP (SEQ ID NOS:1-55 in FIGS. 13A-13B) to determine which were recognized by recSpyCEP antisera. From the data in FIG. 14 we identified 6 putative peptide epitopes having the amino acid sequences set forth on FIG. 15 (S1-6; SEQ ID NOS: 15, 18, 19, 24, 30 and 54). We then made those individual synthetic peptides and conjugated each to DT. Mice were immunized and we showed that the antisera could recognize recSpyCEP, although some were stronger than others (FIGS. 16A-16B). We then performed an IL-8 protection assay and have demonstrated that the anti-peptide antibodies can block the degradation of IL-8 by SpyCEP to varying degrees, but one peptide (S2; SEQ ID NO:18) antiserum can block the degradation of IL8 as effectively as anti-recSpyCEP (FIG. 17). Thus, we have identified the dominant epitope on SpyCEP (SEQ ID NO:18) that can induce functional antibodies.

Data shown in FIGS. 18A-20 tested the immunogenicity of p145, J8 and J8 peptide variants designated as follows:

```
p145
                                            (SEQ ID NO: 56)
LRRDLDASREAKKQVEKALE

J8
                                            (SEQ ID NO: 58)
QAEDKVKQSREAKKQVEKALKQLEDKVQ

J8i V1
                                            (SEQ ID NO: 59)
SREAKKQSREAKKQVEKALKQVEKALC

J8i V2
                                            (SEQ ID NO: 60)
SREAKKQSREAKKQVEKALKQSREAKC

J8i V3
                                            (SEQ ID NO: 61)
SREAKKQVEKALKQSREAKKQVEKALC
```

```
-continued
J8i V4
                                            (SEQ ID NO: 62)
SREAKKQVEKALDASREAKKQVEKALC.
```

Hyperimmune sera were generated in 4-6week old female Balb/c mice following a 28 day immunisation protocol. Mice were immmunised subcutaneously with 30 µg of DT-conjugated peptide (J8, p145, J8iV1, J8iV2, J8iV3 or J8iV4) in PBS and Alum. Immunisations occurred on days 0, 21, 28. Submandibular bleeds to collect blood/sera were performed at days 35, 42 and 49.

We have previously observed that in both mice and humans, antibodies induced by vaccination with J8-DT recognise only poorly the native sequence, p145. We thus designed 4 variant peptides based on the 12-mer J8 insert sequence and designed such that the heptad periodicity of hydrophobic and hydrophilic amino acids was maintained to preserve the alpha-helical structure of the peptide. These are J8iV1, J8iV2, J8iV3 and J8iV4 peptides listed above.

Figure 18A:
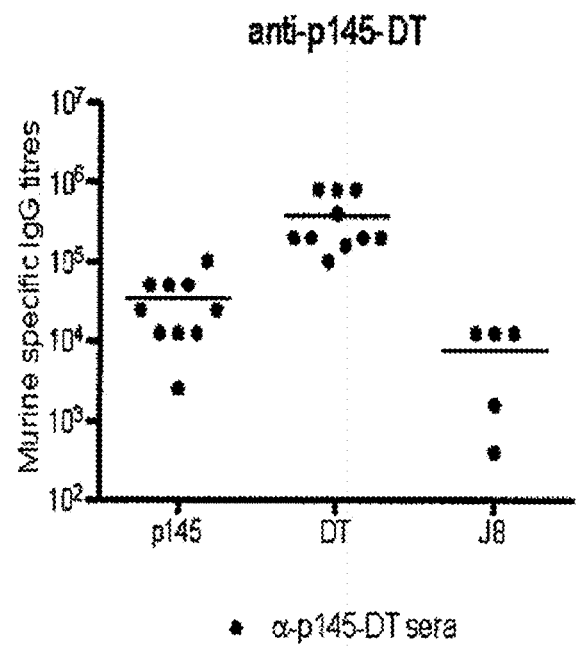
Figure 18B:
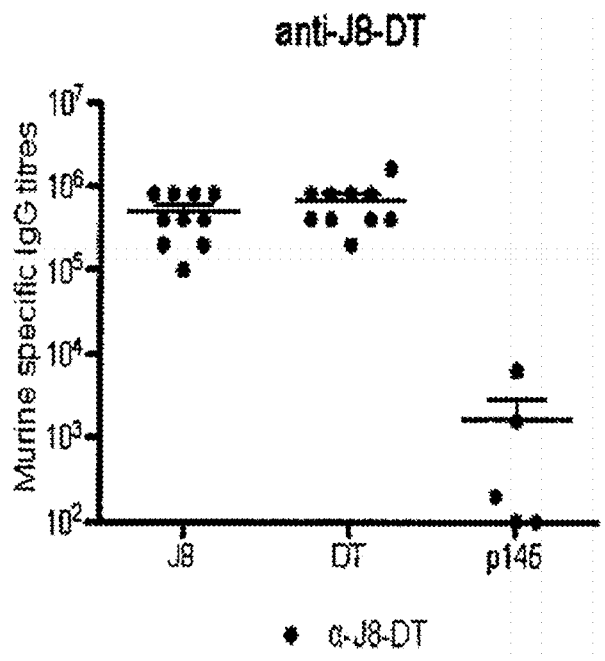
Figure 19A:
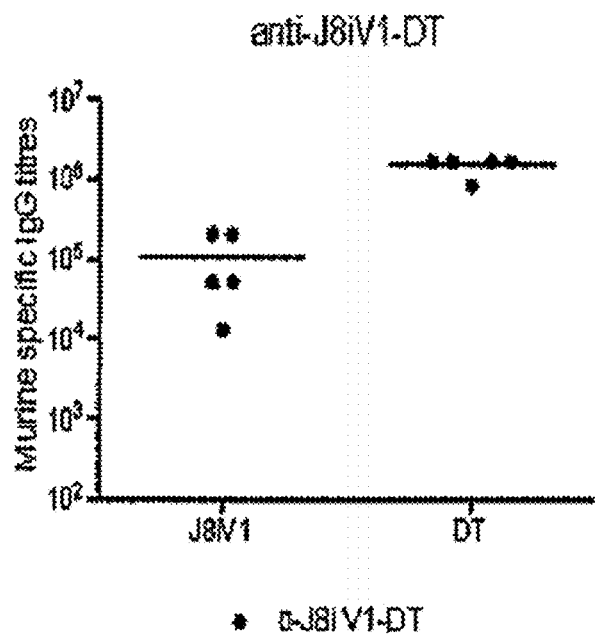
Figure 19B:
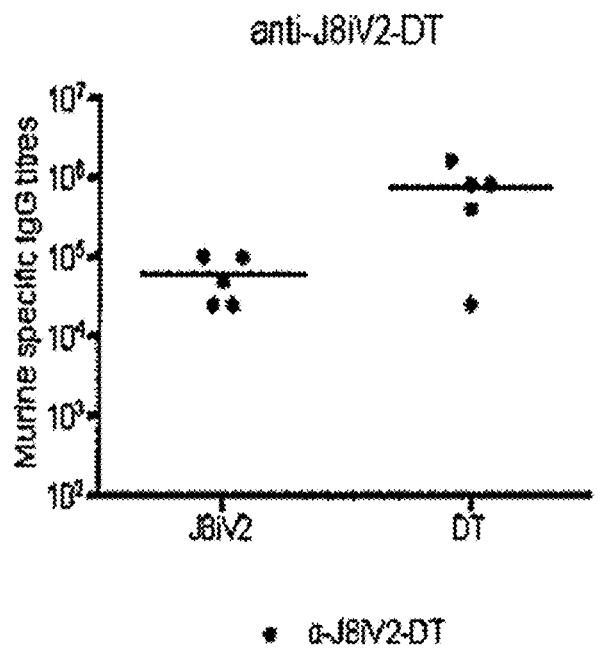
Figure 19C:
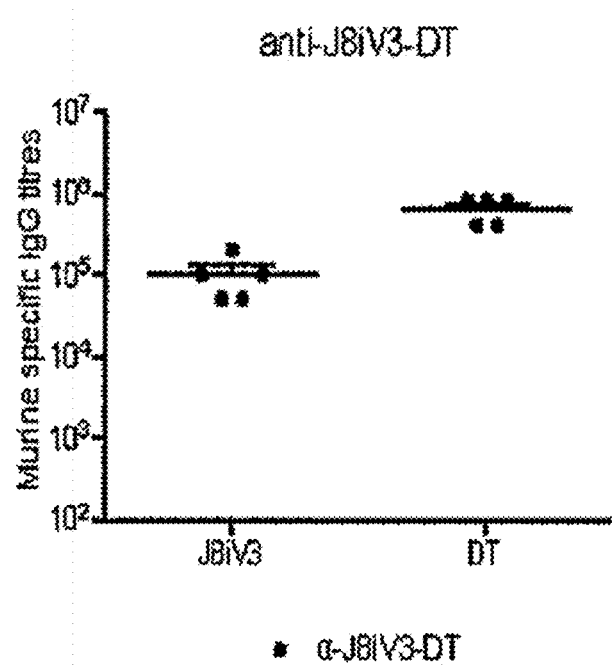
Figure 19D:
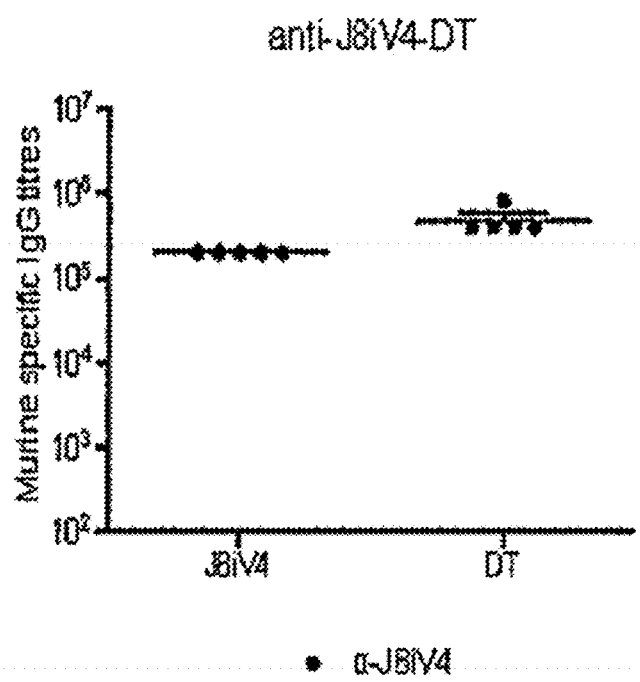

FIG. 18B shows that the titer of p145-specific antibodies induced by J8-DT vaccination is very low (mean about 2000, with some mice below 200). By contrast, the titer of J8-specific antibodies is about 600,000 following J8-DT vaccination. The high titer to J8 must mean that most antibodies are recognizing the non-streptococal flanking sequences at the amino-terminal and carboxyl-terminal segments of J8, although this has not been formally proven.

Figure 20:
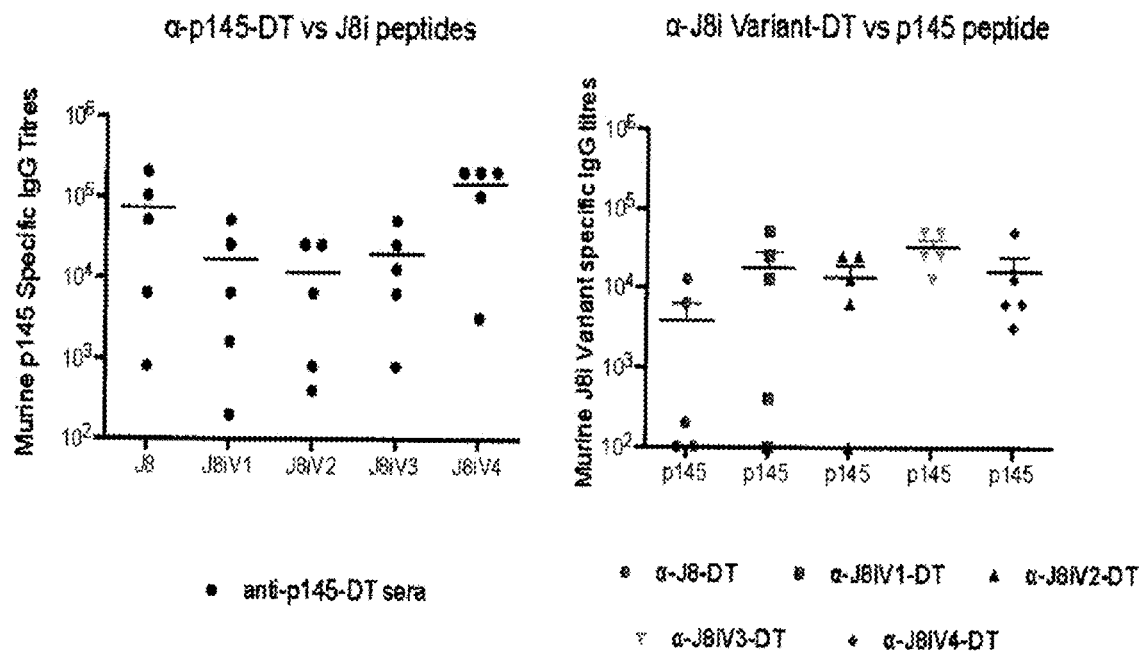

FIGS. 19A-19D show that J8iV1, J8iV2, J8iV3 and J8iV4 all induce high titer antibodies to themselves (approx 100, 000). Importantly, all induce high titers to p145 (>10,000) with J8iV3-DT inducing titers of approximately 30,000 (FIG. 20, right panel). It is probable that the titers of the new peptides to themselves are higher than the titers to p145 because p145 contains additional amino acids not found in the new peptides and some of these may mask the epitopes recognized by the antisera to the new variants. However, the high titers of the variant J8 peptides to themselves (approx 100,000) is significant because they are exclusively derived from streptococcal sequence. Thus, the new variants induce titers of 100,000 with all antibodies recognizing strep sequences, whereas J8 induces streptococcal titers of approximately 2,000.

Figure 21A:
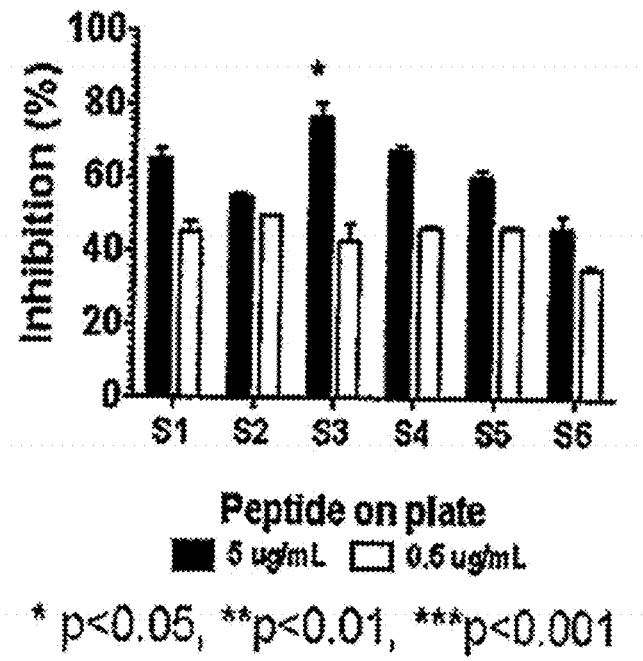
Figure 21B:
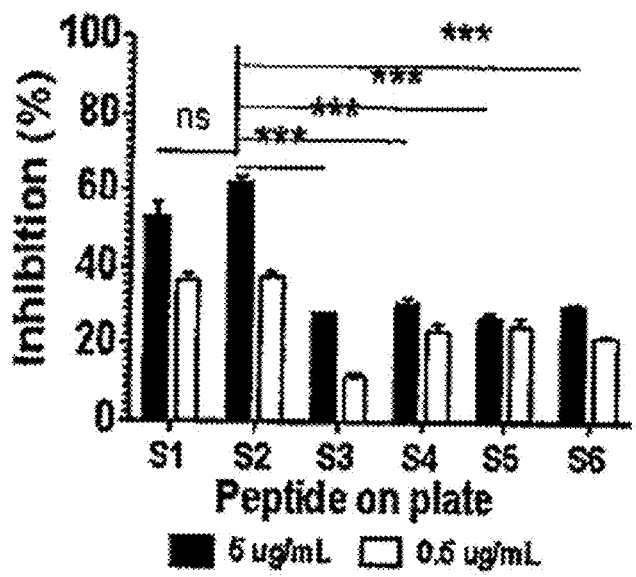
Figure 21C:
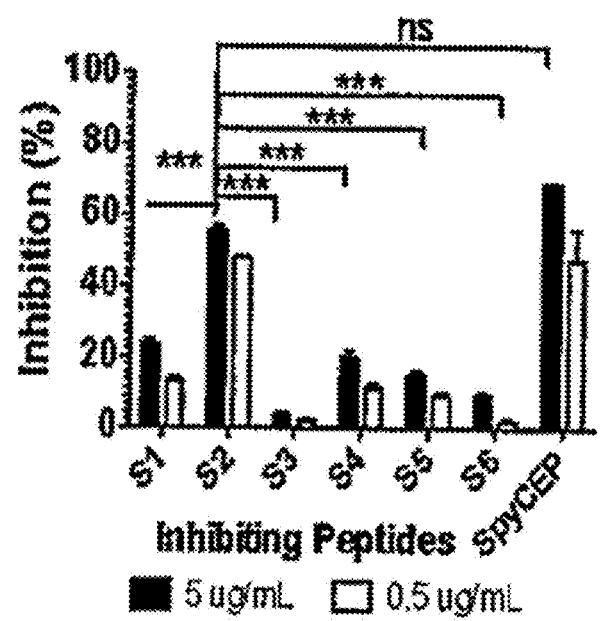

The immunodominance of S2 was further assessed using a peptide inhibition assay. Antisera to recSpyCEP and the individual epitopes were pre-incubated with each of the immunizing antigens after which their binding to the antigen was analysed. The binding of epitope antisera to immobilised self-peptides was greatly reduced following pre-incubation with self-peptide (40-80% inhibition) (FIG. 21A). Pre-incubation of epitope antisera with recSpyCEP also led to inhibition of recognition by immobilised self-peptides with the highest inhibition observed when antiserum to S2-DT was incubated with recSpyCEP (FIG. 21B) indicating that the epitope recognized by S2-DT immunization was displayed on the surface of recSpyCEP. Furthermore, when antiserum to SpyCEP was incubated with each of the 6 peptides we observed that peptide S2 (SEQ ID NO:18) inhibited the binding to the greatest extent and comparably to the inhibition caused by recSpyCEP (FIG. 21C). These data indicate that, in terms of ELISA, the immune response to SpyCEP is defined predominantly by antibody recognition of S2 (SEQ ID NO:18) and that S2 (SEQ ID NO:18) can elicit a similar immune response to the entire recSpyCEP. Thus, S2 (SEQ ID NO:18) is the imunodominant epitope of SpyCEP.

We then tested the binding efficiency of SpyCEP and epitope antisera to various GAS strains. SpyCEP is expressed on the surface of GAS and also shed. To gauge recognition of native antigen, the binding of the different epitope specific antibodies to various GAS strains were compared using a FACS assay. GAS strain 5448 was used alongside with its animal passaged derivative 5448AP (a CovR/S mutant strain known to express high levels of SpyCEP). Similarly, wild-type BSA10 was used in parallel with its animal passaged derivative pBSA10 (also a CovR/S mutant). A reference strain 2031 (emm1) and a Northern Territory of Australia skin isolate, 88/30, were also included. Our data demonstrated that in all cases there was comparable binding to GAS isolates of antibodies induced by vaccination with recSpyCEP to antibodies induced by S2-DT immunization. Antibodies to other epitopes showed variable levels of binding to GAS (FIGS. 22A-22C). In addition, the surface expression of SpyCEP as well as S2 was found to be highest in all the strains tested, as measured by the mean fluorescence intensity (MFI) data (data not shown). These data demonstrate the immunodominance of the S2 epitope on native SpyCEP. However, the data do not demonstrate that antibodies to the S2 epitope would functionally impair the CXC chemokine protease of SpyCEP.

We then asked whether S2-DT could augment the efficacy of the J8-DT vaccine. We have previously demonstrated that recSpyCEP in combination with J8-DT results in significantly better protection against invasive infections with CovR/S mutant strains of GAS than either J8-DT alone or recSpyCEP alone (manuscript submitted). J8-DT and either recSpyCEP or S2-DT were mixed in a ratio of 1:1 by weight and tested in a skin challenge model that we have recently developed (manuscript submitted). Control mice were vaccinated with individual antigens or with PBS. Post-vaccination mice were challenged with 5448AP GAS. Vaccination with J8-DT+S2-DT resulted in significantly reduced bacterial bio-burden in skin as well as in the blood of 5448AP-infected mice (FIGS. 23A-23B). The level of protection offered by J8-DT+S2-DT vaccination was also found to be comparable to that of J8-DT+SpyCEP vaccination. To confirm these findings, the challenge experiments were repeated with another CovR/S mutant strain NS88.2 (FIGS. 24A-24B). Here again we found that vaccination with J8-DT+SpyCEP or J8-DT+S2-DT results in significantly enhanced protective efficacy compared to J8-DT alone. Vaccination with either J8-DT or SpyCEP alone did not offer any protection in comparison to the PBS controls.

Conclusion

Neutrophil activity appears to be a key factor in the efficacy of vaccination with J8 peptide. SpyCEP is an IL-8 degrading protease highly expressed by virulent GAS bacteria such as those having the CovR/S mutation. Immunization with J8 peptide and rSpyCEP in combination had a synergistic effect against GAS infection by the CovR/S GAS mutant 5448AP compared to J8 peptide or SpyCEP alone. It is also evident that anti-SpyCEP antibodies may effectively neutralize the IL-8 degrading activity of SpyCEP, thereby providing a therapeutic intervention for existing GAS infections. Furthermore, we have identified the dominant epitope on SpyCEP (SEQ ID NO:18) that can induce functional antibodies. We are currently planning active and passive vaccine studies with GAS challenge. The advantage of this epitope is that it enables us to avoid using whole recombinant SpyCEP protein in the vaccine, thus improving the safety profile. We believe that the optimal vaccine will be a mixture of J8 and this epitope. In confirmation of this prediction, vaccination with J8-DT+SpyCEP or J8-DT+S2-DT results in significantly enhanced protective efficacy compared to J8-DT alone. Furthermore, variant J8 peptides have been developed which induce high titers to themselves and the streptococcal peptide p145, presumably because they are exclusively derived from streptococcal p145 amino acid sequence.

Throughout this specification, the aim has been to describe the preferred embodiments of the invention without limiting the invention to any one embodiment or specific collection of features. Various changes and modifications may be made to the embodiments described and illustrated herein without departing from the broad spirit and scope of the invention.

All computer programs, algorithms, patent and scientific literature referred to herein is incorporated herein by reference in their entirety.

The invention claimed is:

1. A method of eliciting an immune response to group A streptococcal bacteria in a mammal, said method comprising the step of administering to the mammal an effective amount of a composition comprising an isolated p145 peptide of SEQ ID NO: 56 or an isolated p145 peptide variant that is at least 90% identical to SEQ ID NO: 56 and an isolated SpyCEP peptide of SEQ ID NO: 18 or an isolated SpyCEP peptide variant that is at least 90% identical to SEQ ID NO: 18.

2. The method of claim 1, wherein the SpyCEP peptide facilitates restoring or enhancing neutrophil activity, thereby eliciting the immune response.

3. The method of claim 1, wherein the p145 peptide variant is at least 95% identical to SEQ ID NO: 56.

4. The method of claim 1, wherein the SpyCEP peptide variant is at least 95% identical to SEQ ID NO: 18.

* * * * *